(12) United States Patent
Nagasawa

(10) Patent No.: US 11,717,554 B2
(45) Date of Patent: Aug. 8, 2023

(54) METHOD FOR PREVENTING OR TREATING HANGOVER SYMPTOM(S) ASSOCIATED WITH CONSUMPTION OF ALCOHOLIC BEVERAGE(S)

(71) Applicant: Herbert Nagasawa, Irvine, CA (US)

(72) Inventor: Herbert Nagasawa, Irvine, CA (US)

(73) Assignee: MAX R&D LLC, Pasadena, CA (US)

( * ) Notice: Subject to any disclaimer, the term of this patent is extended or adjusted under 35 U.S.C. 154(b) by 110 days.

(21) Appl. No.: 17/087,517

(22) Filed: Nov. 2, 2020

(65) Prior Publication Data
US 2021/0085746 A1  Mar. 25, 2021

Related U.S. Application Data

(60) Provisional application No. 62/902,558, filed on Sep. 19, 2019.

(51) Int. Cl.
| | | |
|---|---|---|
| A61K 31/145 | (2006.01) | |
| A61K 31/197 | (2006.01) | |
| A61K 31/26 | (2006.01) | |
| A61K 31/385 | (2006.01) | |
| A61K 31/7028 | (2006.01) | |
| A61K 38/05 | (2006.01) | |
| A61P 43/00 | (2006.01) | |

(52) U.S. Cl.
CPC ............ *A61K 38/05* (2013.01); *A61K 31/145* (2013.01); *A61K 31/197* (2013.01); *A61K 31/26* (2013.01); *A61K 31/385* (2013.01); *A61K 31/7028* (2013.01); *A61P 43/00* (2018.01)

(58) Field of Classification Search
CPC combination set(s) only.
See application file for complete search history.

(56) References Cited

U.S. PATENT DOCUMENTS

| | | | | |
|---|---|---|---|---|
| 5,202,354 A | * | 4/1993 | Matsuoka | A61K 31/51 514/474 |
| 2001/0041789 A1 | * | 11/2001 | Nagasawa | C07K 5/06139 548/200 |
| 2005/0267042 A1 | * | 12/2005 | Salaspuro | A61P 39/02 514/561 |
| 2008/0000489 A1 | * | 1/2008 | Suovaniemi | A24D 3/14 131/359 |
| 2010/0239663 A1 | * | 9/2010 | Suovaniemi | A61K 9/2846 514/249 |
| 2011/0033560 A1 | * | 2/2011 | Suovaniemi | A61K 38/05 424/722 |
| 2011/0171296 A1 | * | 7/2011 | Salaspuro | A61K 31/198 424/452 |
| 2018/0161297 A1 | * | 6/2018 | Kirnon | A61K 31/27 |

OTHER PUBLICATIONS

Penning et al., "The Pathology of Alcohol Hangover," Current Drug Abuse Reviews 3:68-75 (2010) (Year: 2010).*
Orrico et al., "Efficacy of D-penicillamine, a sequestering acetaldehyde agent, in the prevention of alcohol relapse-like drinking in rats," Psychopharmacology 228:563-575 (2013) (Year: 2013).*

* cited by examiner

*Primary Examiner* — Julie Ha
*Assistant Examiner* — Kristina M Hellman
(74) *Attorney, Agent, or Firm* — Adriano & Associates

(57) ABSTRACT

The invention provides methods for preventing or treating hangover symptom(s) associated with consumption of alcoholic beverage(s) in a subject comprising administering an aldehyde sequestering agent so as to reduce or counter blood aldehyde buildup in the subject, thereby preventing or treating hangover symptom(s) associated with consumption of alcoholic beverage(s) in the subject.

10 Claims, 3 Drawing Sheets

Figure 1. Chemical Structures of MTCG, BTCG, CG, and CbG
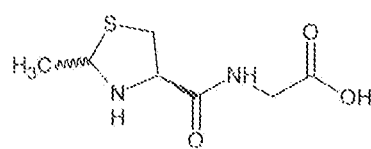
MTCG
(2-Methylthiazolidine-4-carbonylglycine)
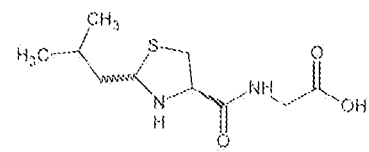
BTCG
(2-Isobutylthiazolidine-4-carbonylglycine)
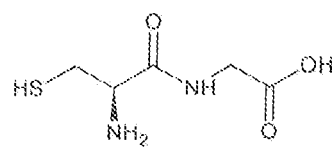
CG
(Cysteinylglycine)
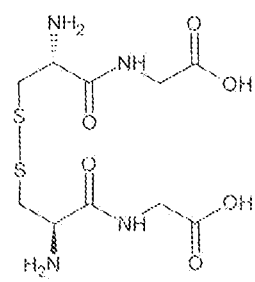
CbG
(Cystinyl-bis-glycine)

Figure 2: MTCG in urine of rats treated with ethanol, disulfiram and CG or CbG
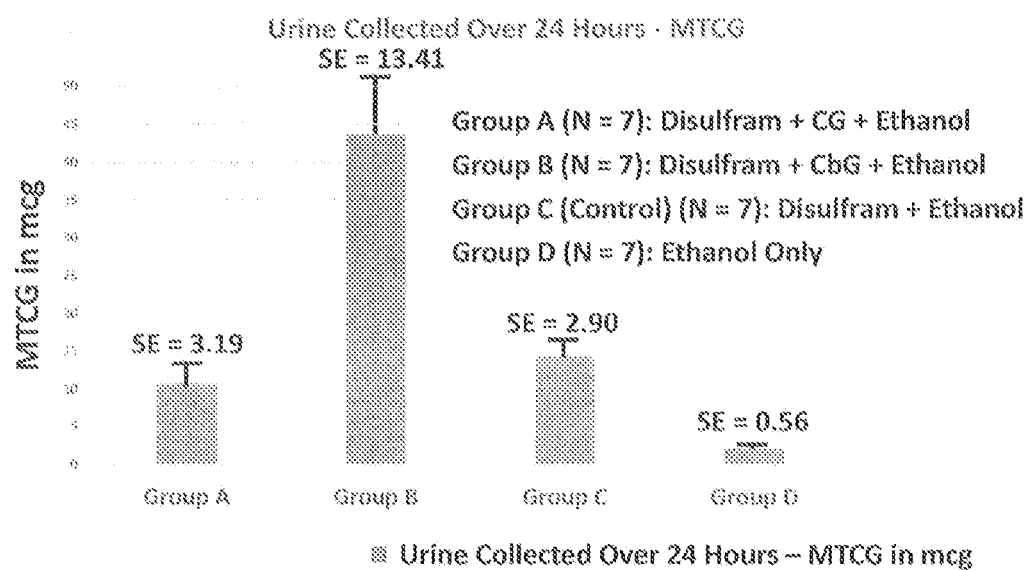

Figure 3: BTCG in urine of rats treated with i-amyl alcohol, cyanamide and CbG
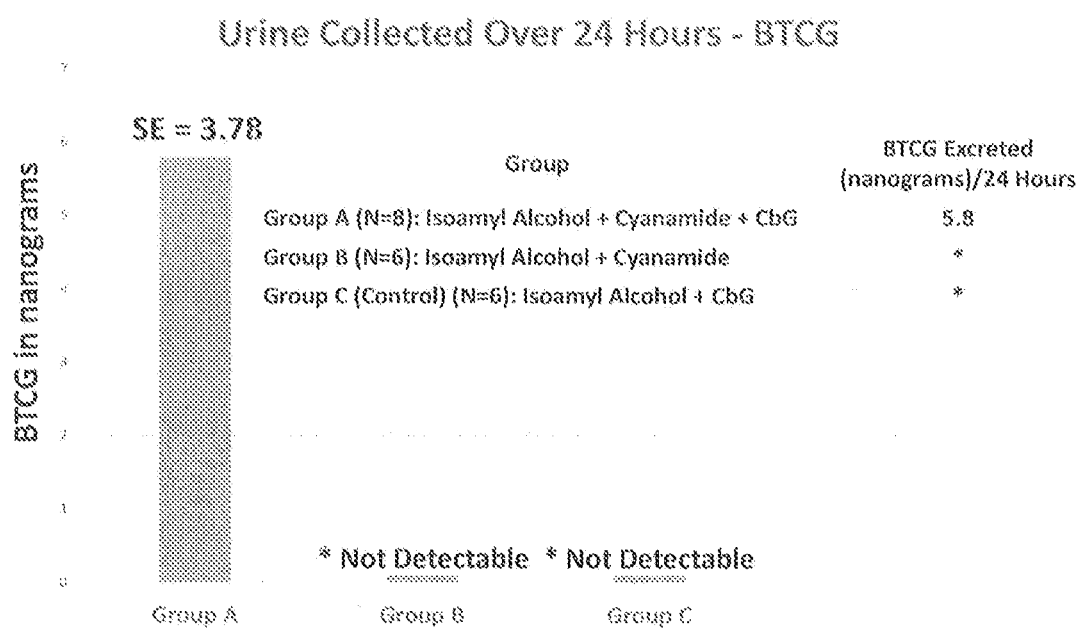

METHOD FOR PREVENTING OR TREATING HANGOVER SYMPTOM(S) ASSOCIATED WITH CONSUMPTION OF ALCOHOLIC BEVERAGE(S)

CROSS REFERENCE TO RELATED APPLICATIONS

The application claims priority to U.S. Provisional Application No. 62/902,558, filed Sep. 19, 2019, which is incorporated herein by reference in its entirety for all purposes.

BACKGROUND OF THE INVENTION

The general public is constantly exposed to a variety of toxic aldehydes, such as formaldehyde, acetaldehyde, glutaraldehyde, and other aldehydes derived from fatty acid oxidation of food and from consumption of alcoholic beverages, which all require an enzyme known as aldehyde dehydrogenase (ALDH) to convert them to their corresponding carboxylic acids, which can then be further metabolized to innocuous products.

Exposure to toxic aldehydes may occur in the workplace, at home, on the road and from smoking or fire. Formaldehyde is used as an embalming chemical, and as a tissue fixation agent in histology laboratories in hospitals. Another occupational hazard is the use of glutaraldehyde in the cold sterilization of heat-sensitive medical equipment. Formaldehyde has also been shown to emanate from inappropriately formulated phenol-formaldehyde resins purchased from overseas suppliers, and used as wallboards, insulation, furnishings and adhesives for homes, causing adverse health effects for occupants. In addition, formaldehyde and acetaldehyde along with aliphatic and aromatic aldehydes are pollutants found in automobile exhaust with the major aldehyde constituent being formaldehyde. Furthermore formaldehyde along with other aldehydes may be found in cigarette smoke as well as may be generated during a fire. Consequently, formaldehyde is usually the most abundant of aldehyde found in urban air followed next by acetaldehyde (for a discussion of aldehydes and formaldehyde as environmental pollutants, see Watson, Ann Y., Bates, Richard R. and Kennedy, Donald, eds. *Air Pollution, the Automobile, and Public Health*, Washington, D.C.: National Academy Press, 1988.

In addition to environmental sources of aldehydes, exposure to aldehydes may occur through the metabolism of ingested fats from food leading to the production of 4-hydroxynonenal (4-HNE), an aldehyde produced by lipid peroxidation, which need to be further oxidized by ALDH to its corresponding carboxylic acid (Chen et al., 2008). Aldehydes may also be ingested directly through added food flavorants such as benzaldehyde associated with bitter almonds and cinnamaldehyde associated with cinnamon bark. Consumption of alcoholic beverages may also directly introduce aldehydes, such as acetaldehyde and furfural, present as congeners, which in order of highest concentration first as found in bourbon and scotch and in one account include: fusel oil, acetic acid, ethyl acetate, acetaldehyde, furfural and tannins (Damrau and Liddy, 1960), or indirectly result in the production of aldehydes from metabolism of alcohol by alcohol dehydrogenase.

One consequence of excess alcoholic beverage consumption is "hangover syndrome," while little or moderate consumption of alcohol may induce pronounced facial flush in a subpopulation of people, primarily of Asian descent.

Hangover Syndrome. Lay magazines and the Internet (Google) are replete with hangover "cures" and recipes for alleviating hangovers, a phenomenon of general feeling of malaise, accompanied by thirst, headache, indigestion, dizziness or fainting, tiredness, loss of appetite, nausea and stomachache (Prat et al., 2009; Rohsenow and Holland, 2010). Hangovers, a morning-after effect, generally follow a bout of excessive drinking of alcoholic beverages such as bourbon, whiskey varieties, wine or beer. Since the common belief that drinking vodka or gin does not lead to hangovers has now been documented by carefully conducted clinical studies with human volunteers under near laboratory settings (Damrau and Liddy, 1960; Rohsenow et al., 2010), investigators have now focused on the potentially toxic congeners known to be found in these alcoholic beverages, such as methanol, as well as acetaldehyde, the first oxidation product of ethanol itself.

The focus on acetaldehyde, the toxic aldehyde produced in the first step of the metabolism of ethanol catalyzed by the enzyme alcohol dehydrogenase (ADH), is based on the well-known "flushing syndrome" exhibited by 30-50% of individuals of Asian descent, who lack a functional enzyme known as aldehyde dehydrogenase (ALDH2) that further metabolizes (oxidizes) the acetaldehyde derived from ethanol to acetate (Nagasawa et al., 1999). As a result, imbibing of even the small quantities of ethanol present in beer or wine by these individuals result in flushing of the face and trunk, and varying degrees of headache, nausea, vertigo, palpitations, tachycardia and (occasionally) hypotension, manifested by the elevation in blood acetaldehyde, and caused by the resultant release of catecholamines and histamine. However, this "flushing syndrome" does not quite mimic—except for headache and nausea—the hangover symptoms described above. Besides, hangovers peak when acetaldehyde is cleared from the blood (Rohsenow and Holland, 2010).

The small amounts of methanol found in alcoholic beverages are generally considered to be innocuous in the presence of the relative overwhelming quantities of ethanol, since much of the methanol can be eliminated in the expired breath or excreted in the urine (Rohsenow and Holland, 2010)). Indeed, ethanol is used as an antidote for severe methanol poisonings (Ekins et al., 1985). This is because the methanol Km for ADH is approximately 10 times larger than the Km for ethanol (Majchrowicz and Mendelson, 1971; Bendtsen et al., 1998), and it cannot itself be metabolized by this enzyme until the concentration of ethanol becomes minimal and equal to or less than the ethanol Km for ADH. Accordingly, blood methanol accumulates with further drinking, especially by chronic drinkers (Kapur et al., 2007), and methanol continues to be excreted in urine even after the clearance of ethanol (Bendtsen et al., 1998). The possibility also exists that another enzyme that metabolizes ethanol known as MEOS (microsomal ethanol oxidizing system, a cytochrome P-450 enzyme of the mixed-function oxidase family) (Lieber, 2004) could oxidize methanol to the toxic formaldehyde. Formaldehyde is further metabolized by formaldehyde dehydrogenase (Strittmatter and Ball, 1955) to formic acid, another toxic product that produces ocular toxicity; hence, the metabolic fate of methanol following the ingestion of an alcoholic beverage is an important issue.

The congeners generally found in bourbon and scotch compared to vodka have been published (Damrau and Liddy, 1960). However, this list is incomplete, and recent data provided by gas chromatographic analyses present a more complete picture of the volatiles (Roth, Part 3, 2011). The congeners found in bourbon and scotch listed by Damrau and Liddy are, in order of highest concentrations first: fusel oil, acetic acid, ethyl acetate, aldehydes (as acetaldehyde), furfural, and tannins.

Fusel Oil

Although there is general consensus among Internet bloggers that the components in fusel oil are the cause of hangovers, there is a paucity of clinical studies on the effects of fusel oil congeners in bourbon and scotch in hangovers, and Wikipedia (updated Aug. 20, 2015) lists only a single study—in animal hangover models (shrew and mice) based on emetic response and taste aversion (Hori et al., 2003). The startling conclusion reached was that "the fusel oil in whiskey alleviates hangovers, contrary to common belief". A Google search under "Fusel oil and hangovers" also did not reveal additional studies. A recent March 2014 article by F. Minnick in Scientific American entitled, "In Search of a Cure for the Dreaded Hangover", merely glosses over fusel oil as just one of the components of congeners. Yet, fusel oil constitutes a major fraction of congeners in bourbon and scotch (Damrau and Liddy, 1960); indeed, 200- to 100-fold more, respectively, than in vodka. And, although "oily", the term "fusel oil" is a misnomer as the components are, in fact, fusel alcohols, and found as residues or "tails" in the distillation of yeast fermentation products of carbohydrates. Accordingly, vodka contains less than 1% of fusel oil compared to bourbon and scotch, and vodkas with much more fusel oil are considered inferior.

The fusel alcohols are comprised mostly of branch-chained primary alcohols higher than ethanol, and are derived from the side-chains of natural amino acids, and, sometimes, from altered pathways (Ingraham, 2010). They are "chiefly, isopentyl (isoamyl) alcohol, 2-methyl-1-butanol, isobutyl alcohol (20%), n-propyl alcohol (3-5%), and small amounts of other alcohols, esters and aldehydes" (Merck Index, 1996). Bourbon contains the highest content of the two isomeric isoamyl alcohols (Roth, Part 3, 2011), and an Internet source also includes "butyl alcohol" and "hexanol" in fusel oil w/o a primary reference citation.

Since these are all aliphatic, primary alcohols, they are subject to oxidation by ADH to their respective aldehydes. One of the aldehydes mentioned in Merck Index may be the already preformed furfural that was listed by Damrau and Liddy (1960). While a list of Km values for ADH for the alcohols listed as components of fusel oil is not available, their Kms, like that for methanol, will likely be much higher than for ethanol itself. This implies (vide supra, re: methanol) that these fusel alcohol congeners in bourbon or scotch cannot be metabolized by ADH in the presence of an abundance of ethanol. Therefore, as one continues to drink more and more bourbon (or the like), these fusel alcohols will accumulate, and can only be accommodated and metabolized by ADH after most of the ethanol is depleted. Moreover, the rate of ethanol metabolism in humans is constant and follows a straight line Widmark's beta (Roth, Part 1, 2011), the total elimination time being dependent on the initial or highest blood concentration of ethanol. In effect, the more one drinks, the longer it will take to bring the blood alcohol levels to near zero—at which point the fusel alcohols can begin to be metabolized by ADH. This is in accord with the observation that at the time of the hangover onset, blood alcohol levels are near zero (Bendtsen et al., 1998; Woo et al., 2004).

Following the excessive drinking of Bourbon and the like, these fusel oil congeners will accumulate until the blood alcohol levels reach near zero, at which point the lower molecular weight fusel alcohols such as the isomeric propyl- and butyl alcohols will start to be metabolized by ALDH to their respective aldehydes or ketones, and then excreted directly in urine or be metabolized further to their carboxylic acids which can be excreted likewise (Bonte and Kuhnholz, 1985). The higher MW fusel alcohols, such as the isomeric amyl alcohols, can be conjugated as the more water-soluble glucuronides and excreted (Bonte and Kuhnholz, 1985).

Asian Flushing Syndrome. It is also known that approximately 40-50% of individuals of Asian descent develop a pronounced facial flush when they consume even a modest amount alcohol. This is because of a dysfunctional aldehyde dehydrogenase (ALDH2) (Geodde and Agrawal, 1987) that prevents the further metabolism of acetaldehyde. The excess circulating acetaldehyde triggers the release of catecholamines and histamine, thus causing the "Asian flush". These Asian are also at risk for heart disease, since they are unable to metabolize 4-HNE from the peroxidation of dietary fats (Chen et al. 2008).

Acetaldehyde (AcH), the aldehyde produced in the first step in the metabolism of ethanol and catalyzed by the enzyme alcohol dehydrogenase (ADH), is toxic because of its high reactivity and propensity to bind to tissue proteins (Medina et al., 1985). Indeed, protein-bound epitopes have been shown to elicit antibody responses to itself (Israel et al., 1986). This ethanol-derived AcH is rapidly metabolized to acetate in the presence of a functional low Km enzyme known as aldehyde dehydrogenase (ALDH2), and since the rate of metabolism of AcH is faster than the formation of AcH from the action of ADH on ethanol, AcH does not accumulate and is present only in minute concentrations in blood. However, about 30 to 50 percent of individuals of Asian descent, viz., Chinese, Japanese, Korean, Vietnamese, Indonesian, much less for Filipina and Thais (northern) but not Asian Indians, develop a conspicuous facial flush when alcohol (ethanol) is consumed (Goedde and Agarwal, 1987). This is due to their lack a functional liver enzyme, ALDH2, where the amino acid at position 487 on this enzyme is replaced by another. The enzyme is present, but its function is drastically reduced because of this inborn error of a point mutation on their ALDH2, wherein the amino acid lysine is substituted for glutamate at this position (Yoshida et al., 1984). As a result, drinking of even the small amounts of ethanol present in beer or wine by these individuals result in flushing of the face and trunk, and varying degrees of headache, nausea, vertigo, palpitations and tachycardia, manifested by the elevation in blood acetaldehyde and caused by the resultant release of catecholamines and histamine.

In recent years, there have been scattered reports on the Internet—some anecdotal—that this "Asian flush" can be attenuated. One word-of-mouth "cure" is to take N-acetyl-L-cysteine (NAC) prior to drinking alcohol. NAC is available over-the-counter as a dietary supplement, and while there may be a basis for this claim, there are no published documents supporting this. NAC liberates L-cysteine when its acetyl group is deacetylated in the liver (Sjoden et al., 1989), and it has been shown that L-cysteine readily combines with acetaldehyde in vitro to MTCA, viz., 2-(R,S)-methylthiazolidine-4(R)-carboxylic acid (Nagasawa et al., 1982). Although Reischl et al. (2012) have shown that MTCA can be found in post mortem blood samples (but, only minimally in urine) from subjects with elevated blood alcohol levels, there is direct evidence indicating that the product formed from acetaldehyde and cysteine, i.e., MTCA, is unstable in vivo and readily disassociates (hydrolytically) to its original components, which are then further metabolized (Nagasawa et al. 1984). Hence, this sequestration of acetaldehyde in vivo by the liberated cysteine from NAC may be only transient. Other reported "cures" for this Asian flush touted on the Internet can be categorically dismissed as lacking any scientific substance.

A need exists for an active agent which is naturally occurring and may be used as a dietary supplement that protects cardiovascular health and/or prevents or inhibits Asian flushing syndrome as well as hangover syndrome. Heretofore, others had concluded that there simply was no cure for hangovers (e.g., Roth, an international authority on alcoholism and hangovers, in a three-part review on "Hangovers", concluded: "There is no cure for a hangover" (Roth; Part 3, 2011)). This discovery addresses that need.

Additionally, a need exists for a safe, effective compound which can sequester toxic aldehyde introduced into a subject following exposure to an aldehyde present in the environment or produced by the subject following metabolism of alcohol and congeners in an alcoholic beverage or metabolism of lipid or fat in food. This discovery also addresses that need.

SUMMARY OF THE INVENTION

The invention provides methods for preventing or treating hangover symptom(s) associated with consumption of alcoholic beverage(s) in a subject. In one embodiment, the method comprises administering an aldehyde sequestering agent so as to reduce or counter blood aldehyde buildup in the subject, thereby preventing or treating hangover symptom(s) associated with consumption of alcoholic beverage(s) in the subject.

The invention also provides methods for preventing or treating hangover symptom(s) associated with ingesting aldehyde(s) and/or fusel oil as congener(s) in alcoholic beverage(s) in a subject. In one embodiment, the method comprises administering an aldehyde sequestering agent so as to reduce or counter blood aldehyde buildup from ingesting aldehyde(s) and/or following metabolism of fusel alcohol(s) to corresponding aldehyde(s) in the subject, thereby preventing or treating hangover symptom(s) associated with consumption (e.g., over or excessive consumption) of alcoholic beverage(s) in the subject.

The invention also provides methods for attenuating facial flushing syndrome associated with consumption of alcoholic beverage(s) in a subject. In one embodiment, the method comprises administering an aldehyde sequestering agent so as to reduce or prevent counter blood acetaldehyde buildup and subsequent release of catecholamine and/or histamine resulting in facial flushing in the subject, thereby attenuating facial flushing syndrome associated with consumption of alcoholic beverage(s) in the subject.

The method further provides methods for decreasing risks of cardiovascular disease or cancer associated with a deficiency of ALDH2 in a subject. In one embodiment, the method comprises administering an aldehyde sequestering agent and/or an agent that functionally increases total activity of ALDH2 so as to reduce or counter aldehyde level in the subject, thereby decreasing risks of cardiovascular disease or cancer associated with a deficiency of ALDH2 in the subject.

The invention provides methods for protecting or treating a subject exposed to environmental or occupational aldehyde(s). In one embodiment, the method comprises administering an aldehyde sequestering agent to the subject so as to sequester the aldehyde(s), thereby protecting or treating a subject exposed to environmental aldehyde(s).

The invention provides a composition comprising an isolated aldehyde sequestering agent and an agent that functionally increases total activity of ALDH2.

The invention provides a composition comprising isolated D-CG or D-CbG, wherein CG or CbG comprises D-cysteine. In another embodiment, the composition further comprises thiamine. The invention also provides a composition comprising isolated CbG, wherein CbG comprises a mixture of D-cysteine and L-cysteine.

BRIEF DESCRIPTION OF DRAWINGS

FIG. 1. Chemical Structures of MTCG, BTCG, CG, and CbG.

FIG. 2. MTCG in urine of rats treated with ethanol, disulfiram and CG or CbG.

FIG. 3. BTCG in urine of rats treated with i-amyl alcohol, cyanamide and CbG

DETAILED DESCRIPTION OF THE INVENTION

Unless defined otherwise, all technical and scientific terms used herein have the same meaning as is commonly understood by one of ordinary skill in the art to which this invention belongs. All patents, applications, published applications and other publications referred to herein are incorporated by reference in their entirety.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more or two or more of the listed items, as well as the lack of combinations when interpreted in the alternative ("or").

As used herein, "one or more" is intended to mean "at least one" or all of the listed elements.

Except where noted otherwise, capitalized and non-capitalized forms of all terms fall within each meaning.

Unless otherwise indicated, it is to be understood that all numbers expressing quantities, ratios, and numerical properties of ingredients, reaction conditions, and so forth used in the specification and claims are contemplated to be able to be modified in all instances by the term "about." As used herein, the term "about" when used before a numerical designation, e.g., temperature, time, amount, concentration, and such other, including a range, indicates approximations which may vary by (+) or (−) 10%, 5% or 1%.

The composition of the invention may be administered in the form of a composition comprising the active agent or ingredient (e.g., an aldehyde sequestering agent so as to reduce or counter blood aldehyde buildup in a subject or an isolated aldehyde sequestering agent and an agent that functionally increases total activity of ALDH2) in an acceptable dosage form. Depending upon the type of disease and patient to be treated, as well as the route of administration, the compositions may be administered at varying doses. Administration may be by methods including, but not limited to, intratumoral delivery, peritumoral delivery, intraperitoneal delivery, intrathecal delivery, intramuscular injection, subcutaneous injection, intravenous delivery, nasal spray and other mucosal delivery (e.g. transmucosal delivery), intra-arterial delivery, intraventricular delivery, intrasternal delivery, intracranial delivery, intradermal injection, electroincorporation (e.g., with electroporation), oncolytic viruses, ultrasound, jet injector, and topical patches.

By "effective amount" as used herein with respect to a vaccine or peptide of the invention, is meant an amount of the vaccine or peptide of the invention, administered to a subject that results in an immune response by the mammal so as to inhibit the disease such as cancer. Further, an effective amount may include any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

A "subject" may be a mammal, and preferably a human. Mammals include, but are not limited to, farm animals (such as cows, sheep, and goats), sport animals, pets (such as cats, dogs and horses), primates (such as, monkeys, gorillas and chimpanzees), mice and rats.

As used herein, "treating" means using a therapy to ameliorate a disorder or condition (e.g., hangover syndrome, disorders associated with exposure to toxic aldehydes, or conditions associated with toxic levels of aldehydes such as 4-HNE produced in the metabolism of lipid peroxides) or one or more of the biological manifestations of the disease or disorder; to directly or indirectly interfere with (a) one or more points in the biological cascade that leads to, or is responsible for, the disease or disorder or (b) one or more of the biological manifestations of the disease or disorder; to alleviate one or more of the symptoms, effects or side effects associated with the disease or disorder or one or more of the symptoms or disorder or treatment thereof; or to slow the progression of the disease or disorder or one or more of the biological manifestations of the disease or disorder. Treatment includes eliciting a clinically significant response. Treatment may also include improving quality of life for a subject afflicted with the disorder or condition. Throughout the specification, compositions of the invention and methods for the use thereof are provided and are chosen to provide suitable treatment for subjects in need thereof, e.g., subjects that inebriated and hungover or suffer from a condition associated with toxic levels of aldehydes such as 4-HNE produced in the metabolism of lipid peroxides.

As used herein, "preventing" is understood to refer to the prophylactic administration of a drug to substantially diminish the likelihood or severity of a condition or biological manifestation thereof, or to delay the onset of such condition or biological manifestation. One skilled in the art will appreciate that prevention is not an absolute term. Prophylactic therapy is appropriate, for example, when a subject is considered at high risk for developing a particular disease or disorder, such as when a subject has a strong family history of a disease or disorder or when a subject has been exposed to e.g., alcohol.

The term "effective amount" means an amount of a compound/composition according to the present invention effective in producing the desired therapeutic effect.

The term "about" means+/−10% of the stipulated value unless indicated otherwise.

The term "treating" a disorder or condition (e.g., hangover symptom(s) associated with consumption of alcoholic beverage(s)), means to manage the disorder or condition with the formulations or compositions of the invention. Treatment can decrease the symptoms of a disorder or condition, reduce the severity of a disorder or condition, alter the course of disorder progression or condition, and/or ameliorate the disorder or condition. The disorder or condition may include but not limited to hangover symptom(s), e.g., typically associated with consumption of alcoholic beverage(s)) n.

In order that the invention herein described may be more fully understood the following description is set forth.

Compositions of the Invention

The invention provides a composition comprising an isolated aldehyde sequestering agent and an agent that functionally increases total activity of ALDH2. The invention also provides a dietary supplement comprising the composition as described above.

In one embodiment, the aldehyde sequestering agent comprises a cysteine moiety comprising a thiol functional group and an amino functional group. In a further embodiment, the thiol functional group and the amino functional group react with an aldehyde to form a cyclic 5-membered thiazolidine derivative. Further, in another embodiment, the thiazolidine derivative is a 2-substituted thiazolidine derivative wherein substituent at position 2 of thiazolidine ring corresponds to side chain of the aldehyde being sequestered.

Examples of the aldehyde sequestering agents include, but are not limited to, cysteinyiglycine (CG), cystinyl-bisglycine (CbG) and a combination thereof. In a further embodiment, reduction of a single molecule of CbG results in production of two molecules of CG. In one embodiment, the amino acid of CG, CbG or a combination thereof is L-amino acid. In another embodiment, the amino acid of CG, CbG or a combination thereof is D-amino acid. In yet another embodiment, the amino acid of CG, CbG or a combination thereof is a mixture of L-amino acid and D-amino acid. In a further embodiment, the amino acid is cysteine of CG or CbG.

In one embodiment, the D-amino acid in CG or CbG results in greater resistance of CG, CbG or reduced CbG to peptidase or dipeptidase than CG or CbG containing only L-amino acid. In a further embodiment, the D-amino acid in CG or CbG results in greater bioavailability of CG, CbG or reduced CbG or longer half-life of CG, CbG or reduced CbG following administration of the aldehyde sequestering agent to the subject.

Examples of the agent that functionally increases total activity of ALDH2 include, but are not limited to, taurine, alpha-lipoic acid, pantethine, 1-isothiocyano-4-(methylsulfinyl)butane (sulforaphane), glucosinolate precursor, glucosinolate, isothiocynate and extract of a cruciferous vegetable or a combination thereof.

In one embodiment of the composition, the agent that functionally increases total activity of ALDH2 is sulforaphane. In another embodiment, the agent that functionally increases total activity of ALDH2 is taurine, alpha-lipoic acid and pantethine. In yet another embodiment, the agent that functionally increases total activity of ALDH2 is taurine, alpha-lipoic acid, pantethine and sulforaphane.

In one embodiment, the composition additionally comprises thiamine or its pharmaceutically acceptable salt. In an embodiment, the pharmaceutically acceptable salt includes, but is not limited to, hydrohalide salt and halide salt.

In one embodiment of the dietary supplement as described above, the amino acid of CG, CbG or a combination thereof is L-amino acid.

In practice, these compounds can be administered in unit dosage form comprising the active ingredient in combination with an acceptable carrier, which can be a solid, semi-solid, or liquid diluent. A unit dosage of the compound can also be administered without a carrier material. Examples of preparations include, but are not limited to, tablets, powders, capsules, aqueous solutions, suspensions including concentrates, liposomes, nano particles and other slow-releasing formulations, as well as transdermal delivery forms. Such techniques are known in the art and may be found in Remington's Pharmaceutical Sciences, Mack Publishing Co., Easton, Pa.

The compounds can be delivered by any suitable means, e.g., topically, orally, parenterally. Preferably, the delivery form is liquid or a solid such as a powder that can be stirred into an ingestible liquid. Standard carriers for topical, oral, or parenteral compositions may be used, many of which are described in Remington's Pharmaceutical Sciences, Mack Publishing Co., Easton, Pa.

For example, for oral administration, suitable carriers or diluents can include mannitol, lactose, starch, silicon dioxide, maltodextrin, citric acid, sodium bicarbonate, lecithin, microcrystalline cellulose, stearic, acid, magnesium stearate, talcum, glucose, and magnesium carbonate.

For parenteral administration, suitable carriers can include water, saline, dextrose, Ringer's solution, glycerol, and the like. Parenteral compositions can be in the form of suspensions, solutions, emulsions, and the like. Parenteral administration is usually by injection or infusion which can be subcutaneous, intramuscular, or intravenous.

The invention further provides a formulation comprising an isolated aldehyde sequestering agent, an agent that functionally increases total activity of ALDH2, and an excipient.

In one embodiment, the formulation is formulated for use as a dietary supplement. In another embodiment, the formulation is formulated for use as a drug.

In one embodiment, the formulation comprises L-CbG. In an additional embodiment, the formulation further comprises thiamine. In another embodiment, the formulation comprises L-CbG and sulforaphane. In yet another embodiment, the formulation comprises L-CbG, taurine, alpha-lipoic acid and pantethine. In a further embodiment, the formulation comprises L-CbG, taurine, alpha-lipoic acid, pantethine, thiamine and/or sulforaphane.

In one embodiment of the formulation, the formulation is a solid formulation. The solid formulation may be a tablet, capsule, caplet, powder, a mixture of pellets or a mixture of granules.

In one embodiment, the solid formulation is an effervescent dosage form. In a further embodiment, the solid formulation is dissolved or mixed with a liquid prior to administration. The liquid may be an alcoholic beverage, juice, soda or water. In one embodiment, the water may be carbonated, flavored or plain.

In one embodiment of the formulation, the solid formulation in an oral dosage form. In another embodiment of the formulation, the formulation is a liquid formulation. In one embodiment, the formulation is a dietary supplement. In another embodiment, the formulation is a drug.

The invention provides a composition comprising isolated D-CG or D-CbG, wherein CG or CbG comprises D-cysteine. In another embodiment, the composition further comprises thiamine. The invention also provides a composition comprising isolated CbG, wherein CbG comprises a mixture of D-cysteine and L-cysteine. In some embodiments, the composition additionally comprises an agent that functionally increases total activity of ALDH2.

In some embodiments, the compositions as described above may be formulated as an oral dosage form. In other embodiments, they may be formulated as a liquid dosage form. In some embodiments, the compositions may be formulated as a drug. In other embodiments, they may be formulated as a dietary supplement.

In some embodiments, the compositions additionally comprise an immediate release component, a controlled-release component or both.

In some embodiments of the compositions as described above, the composition is claimed to promote health, reduce cardiovascular disease, reduce cancer development, prevent or reduce Asian flushing syndrome, prevent or reduce hangover syndrome associated with consumption of alcoholic beverage(s), detoxify aldehyde, clean body system of toxic aldehyde or a combination thereof.

Examples of the agent that functionally increases total activity of ALDH2 include, but are not limited to, taurine, alpha-lipoic acid, pantethine, 1-isothiocyano-4-(methylsulfinyl)butane (sulforaphane), glucosinolate precursor, glucosinolate, isothiocynate and extract of a cruciferous vegetable or a combination thereof.

In one embodiment, the agent that functionally increases total activity of ALDH2 is sulforaphane. In another embodiment, the agent that functionally increases total activity of ALDH2 is taurine, alpha-lipoic acid and pantethine. In yet another embodiment, the agent that functionally increases total activity of ALDH2 is taurine, alpha-lipoic acid, pantethine and sulforaphane. In one embodiment, the agent that functionally increases total activity of ALDH2 is administered with thiamine or its pharmaceutically acceptable salt.

Methods of the Invention

The invention provides methods for preventing or treating hangover symptom(s) associated with consumption of alcoholic beverage(s) in a subject. In one embodiment, the method comprises administering an aldehyde sequestering agent so as to reduce or counter blood aldehyde buildup in the subject, thereby preventing or treating hangover symptom(s) associated with consumption of alcoholic beverage(s) in the subject.

In one embodiment, the alcoholic beverage(s) comprise one or more congener(s). Examples of the congener include, but are not limited to, aldehyde, fusel oil and a combination thereof.

The invention also provides methods for preventing or treating hangover symptom(s) associated with ingesting aldehyde(s) and/or fusel oil as congener(s) in alcoholic beverage(s) in a subject. In one embodiment, the method comprises administering an aldehyde sequestering agent so as to reduce or counter blood aldehyde buildup from ingesting aldehyde(s) and/or following metabolism of fusel alcohol(s) to corresponding aldehyde(s) in the subject, thereby preventing or treating hangover symptom(s) associated with consumption of alcoholic beverage(s) in the subject.

In some embodiments of the invention as described above, the fusel oil comprises a mixture of two or more alcohols. In a further embodiment, the fusel oil is a fermentation product comprising C3 or higher chain length aliphatic alcohols.

In some embodiments of the invention as described above, the fusel oil comprises two or more alcohols. Examples of the two or more alcohol include, but are not limited to, isopentyl (isoamyl) alcohol, 2-methyl-1-butanol, isobutyl alcohol, n-propyl alcohol, butyl alcohol, hexanol and a combination thereof.

In accordance with the practice of the invention, examples of the blood aldehyde include, but are not limited to, aldehyde congener, metabolite of fusel oil and a combination thereof. Examples of the aldehyde congener include, but are not limited to, acetaldehyde, furfural, alkyl aldehyde, aryl aldehyde and a combination thereof. In another embodiment, the metabolite of fusel oil comprises an aldehyde produced enzymatically by alcohol dehydrogenase.

Examples of the aldehyde metabolite of fusel oil include, but are not limited to, 3-methyl-1-butanal, 2-methyl-1-butanal, isobutanal, propanal, butanal, hexanal and a combination thereof.

Examples of the hangover symptom(s) include, but are not limited to, fatigue, weakness, excessive thirst, dry mouth, bad breath, headache, muscle ache, nausea, vomiting, stomach pain, poor sleep, decreased sleep, increased light sensitivity, increased sound sensitivity, dizziness, sense of room spinning, shakiness, decreased ability to concentrate, mood disturbance, depression, anxiety, irritability, and rapid heartbeat, and combination thereof.

In some embodiments of the invention as described above, the hangover symptom(s) occurs following excess consumption of alcoholic beverage(s). In an embodiment, excess consumption of alcoholic beverage(s) results in a blood alcohol level of 0.06% or greater. In another embodiment, excess consumption of alcoholic beverage(s) results in a blood alcohol level of 0.08% or greater. In a separate embodiment, excess consumption of alcoholic beverage(s) results in a blood alcohol level of 0.10% or greater. In another embodiment, excess consumption of alcoholic beverage(s) results in a blood alcohol level of 0.13% or greater. In another embodiment, excess consumption of alcoholic beverage(s) results in a blood alcohol level of 0.16% or greater. In another embodiment, excess consumption of alcoholic beverage(s) results in a blood alcohol level of 0.18% or greater. In another embodiment, excess consumption of alcoholic beverage(s) results in a blood alcohol level of 0.20% or greater. In another embodiment, excess consumption of alcoholic beverage(s) results in a blood alcohol level of 0.24% or greater. In another embodiment, excess consumption of alcoholic beverage(s) results in a blood alcohol level of 0.28% or greater. In another embodiment, excess consumption of alcoholic beverage(s) results in a blood alcohol level of 0.30% or greater. In another embodiment, excess consumption of alcoholic beverage(s) results in a blood alcohol level of 0.34% or greater. In another embodiment, excess consumption of alcoholic beverage(s) results in a blood alcohol level of 0.38% or greater. In another embodiment, excess consumption of alcoholic beverage(s) results in a blood alcohol level of 0.40% or greater. In another embodiment, excess consumption of alcoholic beverage(s) results in a blood alcohol level of 0.44% or greater. In another embodiment, excess consumption of alcoholic beverage(s) results in a blood alcohol level of 0.48% or greater. In another embodiment, excess consumption of alcoholic beverage(s) results in a blood alcohol level between 0.06% and 0.50%.

In another embodiment, excess consumption of alcoholic beverage(s) results in a blood alcohol level between 0.06% and 0.50%. In another embodiment, excess consumption of alcoholic beverage(s) results in a blood alcohol level between 0.06% and 0.099%. In another embodiment, excess consumption of alcoholic beverage(s) results in a blood alcohol level between 0.08% and 0.50%. In another embodiment, excess consumption of alcoholic beverage(s) results in a blood alcohol level between 0.08% and 0.099%. In another embodiment, excess consumption of alcoholic beverage(s) results in a blood alcohol level between 0.100% and 0.199%. In another embodiment, excess consumption of alcoholic beverage(s) results in a blood alcohol level between 0.200% and 0.299%. In another embodiment, excess consumption of alcoholic beverage(s) results in a blood alcohol level between 0.300% and 0.399%. In another embodiment, excess consumption of alcoholic beverage(s) results in a blood alcohol level between 0.400% and 0.500%

In an embodiment, excess consumption of alcoholic beverage(s) produces blunted feelings, reduced sensitivity to pain, euphoria, disinhibition and extraversion or a combination thereof. In an embodiment, excess consumption of alcoholic beverage(s) produces over-expression, boisterousness and possibility of nausea and vomiting or a combination thereof. In an embodiment, excess consumption of alcoholic beverage(s) produces nausea, vomiting, emotional swings, anger or sadness, partial loss of understanding, impaired sensations, decreased libido, possibility of stupor or a combination thereof. In an embodiment, excess consumption of alcoholic beverage(s) produces stupor, central nervous system depression, loss of understanding, lapses in and out of consciousness, and low possibility of death or a combination thereof. In an embodiment, excess consumption of alcoholic beverage(s) produces severe central nervous system depression, coma and possibility of death or a combination thereof.

In an embodiment, excess consumption of alcoholic beverage(s) results in impairment of reasoning, impairment of depth perception, impairment of peripheral vision and impairment of glare recovery or a combination thereof. In an embodiment, excess consumption of alcoholic beverage(s) results in impairment of reflexes, impairment of reaction time, impairment of gross motor control, staggering, slurred speech and temporary erectile dysfunction or a combination thereof. In an embodiment, excess consumption of alcoholic beverage(s) results in severe motor impairment, loss of consciousness and memory blackout or a combination thereof. In an embodiment, excess consumption of alcoholic beverage(s) results in impairment of bladder function, impairment of breathing, disequilibrium and affected heart rate or a combination thereof. In an embodiment, excess consumption of alcoholic beverage(s) results in impairment of breathing, impairment of heart rate, and positional alcohol nystagmus or a combination thereof.

In some other embodiments, the hangover symptom(s) occurs following excess consumption of alcoholic beverage(s) and clearance of ethanol at a blood alcohol level near zero. In an embodiment, a blood alcohol level near zero is a blood alcohol level of 0.04% or lower. In another embodiment, a blood alcohol level near zero is a blood alcohol level of 0.03% or lower. In a separate embodiment, a blood alcohol level near zero is a blood alcohol level of 0.02% or lower. In another embodiment, a blood alcohol level near zero is a blood alcohol level of 0.015% or lower. In another embodiment, a blood alcohol level near zero is a blood alcohol level of 0.010% or lower. In another embodiment, a blood alcohol level near zero is a blood alcohol level of 0.005% or lower. In another embodiment, a blood alcohol level near zero is a blood alcohol level of 0.003% or lower. In another embodiment, a blood alcohol level near zero is a blood alcohol level of 0.001% or lower.

In some other embodiments, the hangover symptom(s) occurs following excess consumption of alcoholic beverage(s) reaching a blood alcohol level of 0.06% or greater and subsequent clearance of ethanol to a blood alcohol level of 0.04% or less. In some other embodiments, the hangover symptom(s) occurs following excess consumption of alcoholic beverage(s) reaching a blood alcohol level of 0.06% or greater and subsequent clearance of ethanol to a blood alcohol level of 0.03% or less. In some other embodiments, the hangover symptom(s) occurs following excess consumption of alcoholic beverage(s) reaching a blood alcohol level of 0.06% or greater and subsequent clearance of ethanol to a blood alcohol level of 0.02% or less. In some other embodiments, the hangover symptom(s) occurs following excess consumption of alcoholic beverage(s) reaching a blood alcohol level of 0.06% or greater and subsequent clearance of ethanol to a blood alcohol level of 0.015% or less. In some other embodiments, the hangover symptom(s) occurs following excess consumption of alcoholic beverage(s) reaching a blood alcohol level of 0.06% or greater and subsequent clearance of ethanol to a blood alcohol level of 0.010% or less. In some other embodiments, the hangover symptom(s) occurs following excess consumption of alcoholic beverage(s) reaching a blood alcohol level of 0.06% or greater and subsequent clearance of ethanol to a blood alcohol level of 0.005% or less. In some other embodiments, the hangover symptom(s) occurs following excess consumption of alcoholic beverage(s) reaching a blood alcohol level of 0.06% or greater and subsequent clearance of ethanol to a blood alcohol level of 0.04% or less. In some other embodiments, the hangover symptom(s) occurs following excess consumption of alcoholic beverage(s) reaching a blood alcohol level of 0.06% or greater and subsequent clearance of ethanol to a blood alcohol level of 0.001% or less.

In some other embodiments, the hangover symptom(s) occurs following excess consumption of alcoholic beverage(s) reaching a blood alcohol level of 0.08% or greater and subsequent clearance of ethanol to a blood alcohol level of 0.04% or less. In some other embodiments, the hangover symptom(s) occurs following excess consumption of alcoholic beverage(s) reaching a blood alcohol level of 0.08% or greater and subsequent clearance of ethanol to a blood alcohol level of 0.03% or less. In some other embodiments, the hangover symptom(s) occurs following excess consumption of alcoholic beverage(s) reaching a blood alcohol level of 0.08% or greater and subsequent clearance of ethanol to a blood alcohol level of 0.02% or less. In some other embodiments, the hangover symptom(s) occurs following excess consumption of alcoholic beverage(s) reaching a blood alcohol level of 0.08% or greater and subsequent clearance of ethanol to a blood alcohol level of 0.015% or less. In some other embodiments, the hangover symptom(s) occurs following excess consumption of alcoholic beverage(s) reaching a blood alcohol level of 0.08% or greater and subsequent clearance of ethanol to a blood alcohol level of 0.010% or less. In some other embodiments, the hangover symptom(s) occurs following excess consumption of alcoholic beverage(s) reaching a blood alcohol level of 0.08% or greater and subsequent clearance of ethanol to a blood alcohol level of 0.005% or less. In some other embodiments, the hangover symptom(s) occurs following excess consumption of alcoholic beverage(s) reaching a blood alcohol level of 0.08% or greater and subsequent clearance of ethanol to a blood alcohol level of 0.003% or less. In some other embodiments, the hangover symptom(s) occurs following excess consumption of alcoholic beverage(s) reaching a blood alcohol level of 0.08% or greater and subsequent clearance of ethanol to a blood alcohol level of 0.001% or less.

In some other embodiments, the hangover symptom(s) occurs following excess consumption of alcoholic beverage(s) reaching a blood alcohol level of 0.10% or greater and subsequent clearance of ethanol to a blood alcohol level of 0.04% or less. In some other embodiments, the hangover symptom(s) occurs following excess consumption of alcoholic beverage(s) reaching a blood alcohol level of 0.10% or greater and subsequent clearance of ethanol to a blood alcohol level of 0.03% or less. In some other embodiments, the hangover symptom(s) occurs following excess consumption of alcoholic beverage(s) reaching a blood alcohol level of 0.10% or greater and subsequent clearance of ethanol to a blood alcohol level of 0.02% or less. In some other embodiments, the hangover symptom(s) occurs following excess consumption of alcoholic beverage(s) reaching a blood alcohol level of 0.10% or greater and subsequent clearance of ethanol to a blood alcohol level of 0.015% or less. In some other embodiments, the hangover symptom(s) occurs following excess consumption of alcoholic beverage(s) reaching a blood alcohol level of 0.10% or greater and subsequent clearance of ethanol to a blood alcohol level of 0.010% or less. In some other embodiments, the hangover symptom(s) occurs following excess consumption of alcoholic beverage(s) reaching a blood alcohol level of 0.10% or greater and subsequent clearance of ethanol to a blood alcohol level of 0.005% or less. In some other embodiments, the hangover symptom(s) occurs following excess consumption of alcoholic beverage(s) reaching a blood alcohol level of 0.10% or greater and subsequent clearance of ethanol to a blood alcohol level of 0.003% or less. In some other embodiments, the hangover symptom(s) occurs following excess consumption of alcoholic beverage(s) reaching a blood alcohol level of 0.10% or greater and subsequent clearance of ethanol to a blood alcohol level of 0.001% or less.

In some other embodiments, the hangover symptom(s) occurs following excess consumption of alcoholic beverage(s) reaching a blood alcohol level of 0.13% or greater and subsequent clearance of ethanol to a blood alcohol level of 0.04% or less. In some other embodiments, the hangover symptom(s) occurs following excess consumption of alcoholic beverage(s) reaching a blood alcohol level of 0.13% or greater and subsequent clearance of ethanol to a blood alcohol level of 0.03% or less. In some other embodiments, the hangover symptom(s) occurs following excess consumption of alcoholic beverage(s) reaching a blood alcohol level of 0.13% or greater and subsequent clearance of ethanol to a blood alcohol level of 0.02% or less. In some other embodiments, the hangover symptom(s) occurs following excess consumption of alcoholic beverage(s) reaching a blood alcohol level of 0.13% or greater and subsequent clearance of ethanol to a blood alcohol level of 0.015% or less. In some other embodiments, the hangover symptom(s) occurs following excess consumption of alcoholic beverage(s) reaching a blood alcohol level of 0.13% or greater and subsequent clearance of ethanol to a blood alcohol level of 0.010% or less. In some other embodiments, the hangover symptom(s) occurs following excess consumption of alcoholic beverage(s) reaching a blood alcohol level of 0.13% or greater and subsequent clearance of ethanol to a blood alcohol level of 0.005% or less. In some other embodiments, the hangover symptom(s) occurs following excess consumption of alcoholic beverage(s) reaching a blood alcohol level of 0.13% or greater and subsequent clearance of ethanol to a blood alcohol level of 0.003% or less. In some other embodiments, the hangover symptom(s) occurs following excess consumption of alcoholic beverage(s) reaching a blood alcohol level of 0.13% or greater and subsequent clearance of ethanol to a blood alcohol level of 0.001% or less.

In some other embodiments, the hangover symptom(s) occurs following excess consumption of alcoholic beverage(s) reaching a blood alcohol level of 0.16% or greater and subsequent clearance of ethanol to a blood alcohol level of 0.04% or less. In some other embodiments, the hangover symptom(s) occurs following excess consumption of alcoholic beverage(s) reaching a blood alcohol level of 0.16% or greater and subsequent clearance of ethanol to a blood alcohol level of 0.03% or less. In some other embodiments, the hangover symptom(s) occurs following excess consumption of alcoholic beverage(s) reaching a blood alcohol level of 0.16% or greater and subsequent clearance of ethanol to a blood alcohol level of 0.02% or less. In some other embodiments, the hangover symptom(s) occurs following excess consumption of alcoholic beverage(s) reaching a blood alcohol level of 0.16% or greater and subsequent clearance of ethanol to a blood alcohol level of 0.015% or less. In some other embodiments, the hangover symptom(s) occurs following excess consumption of alcoholic beverage(s) reaching a blood alcohol level of 0.16% or greater and subsequent clearance of ethanol to a blood alcohol level of 0.010% or less. In some other embodiments, the hangover symptom(s) occurs following excess consumption of alcoholic beverage(s) reaching a blood alcohol level of 0.16% or greater and subsequent clearance of ethanol to a blood alcohol level of 0.005% or less. In some other embodiments, the hangover symptom(s) occurs following excess consumption of alcoholic beverage(s) reaching a blood alcohol level of 0.16% or greater and subsequent clearance of ethanol to a blood alcohol level of 0.003% or less. In some other embodiments, the hangover symptom(s) occurs following excess consumption of alcoholic beverage(s) reaching a blood alcohol level of 0.16% or greater and subsequent clearance of ethanol to a blood alcohol level of 0.001% or less.

In some other embodiments, the hangover symptom(s) occurs following excess consumption of alcoholic beverage(s) reaching a blood alcohol level of 0.18% or greater and subsequent clearance of ethanol to a blood alcohol level of 0.04% or less. In some other embodiments, the hangover symptom(s) occurs following excess consumption of alcoholic beverage(s) reaching a blood alcohol level of 0.18% or greater and subsequent clearance of ethanol to a blood alcohol level of 0.03% or less. In some other embodiments, the hangover symptom(s) occurs following excess consumption of alcoholic beverage(s) reaching a blood alcohol level of 0.18% or greater and subsequent clearance of ethanol to a blood alcohol level of 0.02% or less. In some other embodiments, the hangover symptom(s) occurs following excess consumption of alcoholic beverage(s) reaching a blood alcohol level of 0.18% or greater and subsequent clearance of ethanol to a blood alcohol level of 0.015% or less. In some other embodiments, the hangover symptom(s) occurs following excess consumption of alcoholic beverage(s) reaching a blood alcohol level of 0.18% or greater and subsequent clearance of ethanol to a blood alcohol level of 0.010% or less. In some other embodiments, the hangover symptom(s) occurs following excess consumption of alcoholic beverage(s) reaching a blood alcohol level of 0.18% or greater and subsequent clearance of ethanol to a blood alcohol level of 0.005% or less. In some other embodiments, the hangover symptom(s) occurs following excess consumption of alcoholic beverage(s) reaching a blood alcohol level of 0.18% or greater and subsequent clearance of ethanol to a blood alcohol level of 0.003% or less. In some other embodiments, the hangover symptom(s) occurs following excess consumption of alcoholic beverage(s) reaching a blood alcohol level of 0.18% or greater and subsequent clearance of ethanol to a blood alcohol level of 0.001% or less.

In some other embodiments, the hangover symptom(s) occurs following excess consumption of alcoholic beverage(s) reaching a blood alcohol level of 0.20% or greater and subsequent clearance of ethanol to a blood alcohol level of 0.04% or less. In some other embodiments, the hangover symptom(s) occurs following excess consumption of alcoholic beverage(s) reaching a blood alcohol level of 0.20% or greater and subsequent clearance of ethanol to a blood alcohol level of 0.03% or less. In some other embodiments, the hangover symptom(s) occurs following excess consumption of alcoholic beverage(s) reaching a blood alcohol level of 0.20% or greater and subsequent clearance of ethanol to a blood alcohol level of 0.02% or less. In some other embodiments, the hangover symptom(s) occurs following excess consumption of alcoholic beverage(s) reaching a blood alcohol level of 0.20% or greater and subsequent clearance of ethanol to a blood alcohol level of 0.015% or less. In some other embodiments, the hangover symptom(s) occurs following excess consumption of alcoholic beverage(s) reaching a blood alcohol level of 0.20% or greater and subsequent clearance of ethanol to a blood alcohol level of 0.010% or less. In some other embodiments, the hangover symptom(s) occurs following excess consumption of alcoholic beverage(s) reaching a blood alcohol level of 0.20% or greater and subsequent clearance of ethanol to a blood alcohol level of 0.005% or less. In some other embodiments, the hangover symptom(s) occurs following excess consumption of alcoholic beverage(s) reaching a blood alcohol level of 0.20% or greater and subsequent clearance of ethanol to a blood alcohol level of 0.003% or less. In some other embodiments, the hangover symptom(s) occurs following excess consumption of alcoholic beverage(s) reaching a blood alcohol level of 0.20% or greater and subsequent clearance of ethanol to a blood alcohol level of 0.001% or less.

In some other embodiments, the hangover symptom(s) occurs following excess consumption of alcoholic beverage(s) reaching a blood alcohol level of 0.24% or greater and subsequent clearance of ethanol to a blood alcohol level of 0.04% or less. In some other embodiments, the hangover symptom(s) occurs following excess consumption of alcoholic beverage(s) reaching a blood alcohol level of 0.24% or greater and subsequent clearance of ethanol to a blood alcohol level of 0.03% or less. In some other embodiments, the hangover symptom(s) occurs following excess consumption of alcoholic beverage(s) reaching a blood alcohol level of 0.24% or greater and subsequent clearance of ethanol to a blood alcohol level of 0.02% or less. In some other embodiments, the hangover symptom(s) occurs following excess consumption of alcoholic beverage(s) reaching a blood alcohol level of 0.24% or greater and subsequent clearance of ethanol to a blood alcohol level of 0.015% or less. In some other embodiments, the hangover symptom(s) occurs following excess consumption of alcoholic beverage(s) reaching a blood alcohol level of 0.24% or greater and subsequent clearance of ethanol to a blood alcohol level of 0.010% or less. In some other embodiments, the hangover symptom(s) occurs following excess consumption of alcoholic beverage(s) reaching a blood alcohol level of 0.24% or greater and subsequent clearance of ethanol to a blood alcohol level of 0.005% or less. In some other embodiments, the hangover symptom(s) occurs following excess consumption of alcoholic beverage(s) reaching a blood alcohol level of 0.24% or greater and subsequent clearance of ethanol to a blood alcohol level of 0.003% or less. In some other embodiments, the hangover symptom(s) occurs following excess consumption of alcoholic beverage(s) reaching a blood alcohol level of 0.24% or greater and subsequent clearance of ethanol to a blood alcohol level of 0.001% or less.

In some other embodiments, the hangover symptom(s) occurs following excess consumption of alcoholic beverage(s) reaching a blood alcohol level of 0.28% or greater and subsequent clearance of ethanol to a blood alcohol level of 0.04% or less. In some other embodiments, the hangover symptom(s) occurs following excess consumption of alcoholic beverage(s) reaching a blood alcohol level of 0.28% or greater and subsequent clearance of ethanol to a blood alcohol level of 0.03% or less. In some other embodiments, the hangover symptom(s) occurs following excess consumption of alcoholic beverage(s) reaching a blood alcohol level of 0.28% or greater and subsequent clearance of ethanol to a blood alcohol level of 0.02% or less. In some other embodiments, the hangover symptom(s) occurs following excess consumption of alcoholic beverage(s) reaching a blood alcohol level of 0.28% or greater and subsequent clearance of ethanol to a blood alcohol level of 0.015% or less. In some other embodiments, the hangover symptom(s) occurs following excess consumption of alcoholic beverage(s) reaching a blood alcohol level of 0.28% or greater and subsequent clearance of ethanol to a blood alcohol level of 0.010% or less. In some other embodiments, the hangover symptom(s) occurs following excess consumption of alcoholic beverage(s) reaching a blood alcohol level of 0.28% or greater and subsequent clearance of ethanol to a blood alcohol level of 0.005% or less. In some other embodiments, the hangover symptom(s) occurs following excess consumption of alcoholic beverage(s) reaching a blood alcohol level of 0.28% or greater and subsequent clearance of ethanol to a blood alcohol level of 0.003% or less. In some other embodiments, the hangover symptom(s) occurs following excess consumption of alcoholic beverage(s) reaching a blood alcohol level of 0.28% or greater and subsequent clearance of ethanol to a blood alcohol level of 0.001% or less.

In some other embodiments, the hangover symptom(s) occurs following excess consumption of alcoholic beverage(s) reaching a blood alcohol level of 0.30% or greater and subsequent clearance of ethanol to a blood alcohol level of 0.04% or less. In some other embodiments, the hangover symptom(s) occurs following excess consumption of alcoholic beverage(s) reaching a blood alcohol level of 0.30% or greater and subsequent clearance of ethanol to a blood alcohol level of 0.03% or less. In some other embodiments, the hangover symptom(s) occurs following excess consumption of alcoholic beverage(s) reaching a blood alcohol level of 0.30% or greater and subsequent clearance of ethanol to a blood alcohol level of 0.02% or less. In some other embodiments, the hangover symptom(s) occurs following excess consumption of alcoholic beverage(s) reaching a blood alcohol level of 0.30% or greater and subsequent clearance of ethanol to a blood alcohol level of 0.015% or less. In some other embodiments, the hangover symptom(s) occurs following excess consumption of alcoholic beverage(s) reaching a blood alcohol level of 0.30% or greater and subsequent clearance of ethanol to a blood alcohol level of 0.010% or less. In some other embodiments, the hangover symptom(s) occurs following excess consumption of alcoholic beverage(s) reaching a blood alcohol level of 0.30% or greater and subsequent clearance of ethanol to a blood alcohol level of 0.005% or less. In some other embodiments, the hangover symptom(s) occurs following excess consumption of alcoholic beverage(s) reaching a blood alcohol level of 0.30% or greater and subsequent clearance of ethanol to a blood alcohol level of 0.003% or less. In some other embodiments, the hangover symptom(s) occurs following excess consumption of alcoholic beverage(s) reaching a blood alcohol level of 0.30% or greater and subsequent clearance of ethanol to a blood alcohol level of 0.001% or less.

Examples of the aldehyde sequestering agent include, but are not limited to, CG, CbG and a combination thereof. In one embodiment, the cysteine in CG or CbG may be L-cysteine. In another embodiment, the CG or CbG is L-cysteinylglycine or L-cystinyl-bis-glycine, respectively. In another embodiment, the cysteine in CG or CbG may be D-cysteine. In yet another embodiment, the CG or CbG is D-cysteinylglycine or D-cystinyl-bis-glycine, respectively. Yet in another embodiment, the cysteine in CbG is a mixture of L-cysteine and D-cysteine. Further, in another embodiment, the CbG is DL-cystinyl-bis-glycine. In a preferred embodiment, the cysteine in CG or CbG is L-cysteine. In a preferred embodiment, the CG or CbG is L-cysteinylglycine or L-cystinyl-bis-glycine, respectively.

In accordance with the practice of the invention, the methods for preventing or treating hangover symptom(s) associated with consumption of alcoholic beverage(s) and associated with ingesting aldehyde(s) and/or fusel oil as congener(s) in alcoholic beverage(s) in a subject may additionally comprise administering taurine, alpha-lipoic acid, pantethine, thiamine, 1-isothiocyano-4-(methylsulfinyl)butane (sulforaphane), glucosinolate precursor, glucosinolate, isothiocynate and extract of a cruciferous vegetable or a combination thereof. In a further embodiment, the combination increases total activity of aldehyde dehydrogenase in the subject.

In one embodiment of the method, the taurine, alpha-lipoic acid, pantethine, thiamine, 1-isothiocyano-4-(methylsulfinyl)butane (sulforaphane), glucosinolate precursor, glucosinolate, isothiocynate and extract of a cruciferous vegetable or a combination thereof may be administered as a dietary supplement. In another embodiment, the taurine, alpha-lipoic acid, pantethine, thiamine, 1-isothiocyano-4-(methylsulfinyl)butane (sulforaphane), glucosinolate precursor, glucosinolate, isothiocynate and extract of a cruciferous vegetable or a combination thereof is formulated with the aldehyde sequestering agent. In one embodiment, the formulation is a dietary supplement. In another embodiment, the formulation is a drug.

In some embodiments of the methods of the invention as described above, the formulation of the dietary supplement or the drug additionally comprises an immediate release component, a controlled release component or both.

In one embodiment, the taurine, alpha-lipoic acid, pantethine, thiamine, 1-isothiocyano-4-(methylsulfinyl)butane (sulforaphane), glucosinolate precursor, glucosinolate, isothiocynate and extract of a cruciferous vegetable or a combination thereof may be administered together with the aldehyde sequestering agent at the same time. In another embodiment, they are administered separately from the aldehyde sequestering agent. In yet another embodiment, they are administered separately but at the same time, before or after administration of the aldehyde sequestering agent.

Examples of the cruciferous vegetable include, but are not limited to, broccoli, broccoli sprouts, broccoflower, broccoli Romanesco, wild broccoli, cauliflower, brussels sprouts, cabbage, green cabbage, red cabbage, Savoy cabbage, wrapped heart mustard cabbage, Chinese cabbage, napa cabbage, choy sum, kale, Siberian kale, radish, turnip, lad cress, horseradish, Ethiopian mustard, mustard seed, mustard green, brown mustard seed, green mustard seed, white mustard seed, black mustard seed, collard green, Chinese broccoli, bok choy, kohlrabi, komatsuna, mizuna, rapini, turnip root, daikon, rutabaga, canola, rape seed, Tatsoi, wild arugula, arugula, field pepperweed, maca, garden cress, watercress and wasabi.

The cruciferous vegetable belongs to a genus. Examples of the genus include, but are not limited to, *Armoracia, Barbarea, Brassica, Diplotaxis, Eruca, Lepidium, Nasturtium, Raphanus* and *Wasabia*.

Examples of the cruciferous vegetable include, but are not limited to, *Armoracia Rusticana, Barbarea verna, Brassica carinata, Brassica oleracea, Brassica rapa, Brassica napus, Brassica juncea, Brassica hirta, Brassica nigra, Brassica rosularis, Diplotaxis tenuifolia, Eruca vesicaria, Lepidium campestre, Lepidium meyenii, Lepidium sativum, Nasturtium officinale, Raphanus sativus* and *Wasabia japonica*.

In one embodiment, the glucosinolate precursor, glucosinolate or extract of a cruciferous vegetable induces induction of an aldehyde dehydrogenase gene in the subject. In a further embodiment, induction of an aldehyde dehydrogenase gene increases total activity of aldehyde dehydrogenase in the subject.

In another embodiment, the extract of cruciferous vegetable comprises a glucosinolate precursor, glucosinolate, 1-isothiocyano-4-(methylsulfinyl)butane (sulforaphane) or a combination thereof.

Examples of the glucosinolate include, but are not limited to, glucobrassicin, neoglucobrassicin, methoxyglucobrassicin, gluconastutiin, sinigrin, progoitrin and glucoraphanin. Glucosinolate may be an indolyl glucosinolate, a phenyl glucosinolate or an aliphatic glucosinolate. Examples of indolyl glucosinolates include, but are not limited to, glucobrassicin, neoglucobrassicin and methoxyglucobrassicin. Examples of phenyl glucosinolates include, but are not limited to, glucotropaeolin (benzylglucosinolate) and gluconasturtiin (2-phenylethylglucosinolate). Examples of aliphatic glucosinolates include, but are not limited to, sinigrin, progoitrin and glucoraphanin. In a preferred embodiment the glucosinolate may be an aliphatic glucosinolate. In another embodiment, the preferred aliphatic glucosinolate is glucoraphanin. In one embodiment, the glucoraphanin is hydrolyzed to 1-isothiocyano-4-(methylsulfinyl)butane (sulforaphane).

In some embodiments, the glycosinolate may be hydrolyzed to produce isothiocynate. Examples of the isothiocynate include, but are not limited to, 1-isothiocyano-4-(methylsulfinyl)butane (sulforaphane), allyl isothiocyanate, benzyl isothiocyanate and phenethyl isothiocyanate. In one embodiment, the isothiocynate is bioactive. In a preferred embodiment, the isothiocynate may be 1-isothiocyano-4-(methylsulfinyl)butane (sulforaphane). In a further embodiment, the bioactivity of isothiocynate increases total aldehyde dehydrogenase activity in the subject. Examples of the aldehyde dehydrogenase include, but are not limited to, aldehyde dehydrogenase 1 and aldehyde dehydrogenase 2. In another further embodiment, the bioactivity of isothiocynate reduces or counters aldehyde level in the subject.

In some embodiments, the sulforaphane increases total aldehyde dehydrogenase activity in the subject. In a further embodiment, the aldehyde dehydrogenase is ALDH2.

In some embodiments of the invention as described above, the aldehyde sequestering agent forms a covalent adduct with aldehyde congener and/or aldehyde metabolite of fusel oil. In a further embodiment, the covalent adduct is a cyclic 5-membered thiazolidine derivative. In yet a further embodiment, the thiazolidine derivative is a 2-substituted thiazolidine derivative wherein substituent at position 2 of thiazolidine ring corresponds to side chain of the aldehyde being sequestered. In another embodiment, the covalent adduct formed between an acetaldehyde congener and cysteinylglycine (CG) or cystinyl-bis-glycine (CbG) is 2-methylthiazolidine-4-carbonylglycine (MTCG). In yet another embodiment, the covalent adduct formed between an isoamyl aldehyde metabolite from metabolism of isoamyl alcohol congener and CG or CbG is 2-isobutylthiazolidine-4-carbonylglycine (BTCG).

In one embodiment, the covalent adduct may be detected in bile or urine of the subject. In another embodiment, the covalent adduct may be detected in urine of the subject.

In some embodiments of the invention as described above, the aldehyde sequestering agent is administered as a dietary supplement. Examples of the aldehyde sequestering agent in the dietary supplement include, but are not limited to, CG, CbG or a combination thereof. In one embodiment, the aldehyde sequestering agent is CbG. Examples of the amino acid(s) of CG or CbG include, but are not limited to, L-amino acid, D-amino acid or a combination thereof. In one embodiment, the amino acid(s) is L-amino acid. In another embodiment, the amino acid(s) is D-amino acid. In yet another embodiment, the amino acid(s) is a mixture of L-amino acid and D-amino acid. In a preferred embodiment, the amino acid(s) is L-amino acid.

In one embodiment, the dietary supplement may additionally comprise taurine, alpha-lipoic acid, pantethine, thiamine, 1-isothiocyano-4-(methylsulfinyl)butane (sulforaphane), glucosinolate precursor, glucosinolate, isothiocynate and extract of a cruciferous vegetable or a combination thereof.

In accordance with the practice of the invention, the dietary supplement is taken by a subject at risk of developing hangover symptom(s). In one embodiment, the dietary supplement is taken before, during or after consumption of alcoholic beverage(s).

In some embodiments of the invention as described above, the dietary supplement is taken prior to reaching blood alcohol level near zero following excess alcoholic beverage consumption sufficient to produce a hangover syndrome in the subject.

In some embodiments of the invention as described above, the dietary supplement is taken before bedtime following an evening of excessive consumption of alcoholic beverage(s) sufficient to produce a hangover syndrome in the subject.

In accordance with the practice of the invention, the aldehyde sequestering agent is administered to or by a subject at risk of developing hangover symptom(s). In one embodiment, the aldehyde sequestering agent is administered before, during or after consumption of alcoholic beverage(s). In another embodiment, the aldehyde sequestering agent is administered prior to reaching blood alcohol level near zero following excess alcoholic beverage consumption sufficient to produce a hangover syndrome in the subject. Embodiments of excess alcoholic beverage consumption may be found above (vide supra). In yet another embodiment, the aldehyde sequestering agent is administered following an evening of excessive consumption of alcoholic beverage(s) sufficient to produce a hangover syndrome in the subject. Embodiments of hangover syndrome may be found above (vide supra).

In some embodiments of the invention as described above, the aldehyde sequestering agent is formulated to be administered as a dietary supplement. In other embodiments of the invention as described above, the aldehyde sequestering agent is formulated to be administered as a drug. Examples of the aldehyde sequestering agent include, but are not limited to, CG, CbG or a combination thereof. In one embodiment, the dietary supplement additionally comprises taurine, alpha-lipoic acid, pantethine, thiamine, 1-isothiocyano-4-(methylsulfinyl)butane (sulforaphane), glucosinolate precursor, glucosinolate, isothiocynate and extract of a cruciferous vegetable or a combination thereof.

In some embodiments of the invention as described above, the blood aldehyde buildup comprises aldehyde congeners and/or aldehydes produced from metabolism of fusel oil. In other embodiments of the invention as described above, the blood aldehyde buildup consists of aldehyde congeners and/or aldehydes produced from metabolism of fusel oil. In further embodiments, the aldehydes produced from metabolism of fusel oil may be aldehydes with 3 or more carbon chain length. In other embodiments, the aldehydes produced from metabolism of fusel oil may be aldehydes with 6 or fewer carbon chain length. In yet some other embodiments, the aldehydes produced from metabolism of fusel oil may be aldehydes having a carbon chain length between 3 and 6 carbons.

In some embodiments of the invention as described above, the aldehyde associated with a hangover syndrome is an aldehyde having a carbon chain length of more than 2 carbons. In other embodiments, the aldehyde associated with a hangover syndrome is an aldehyde having hydrophobicity greater than hydrophobicity of an acetaldehyde.

In some embodiments of the invention as described above, the blood aldehyde buildup blood associated hangover syndrome and metabolism of fusel oil occurs at a time after decline of blood ethanol level to zero or near zero from a peak blood ethanol level from consumption of alcoholic beverage(s). In some embodiments, near zero from a peak blood ethanol level may be a blood alcohol level of 0.04% or lower. In another embodiment, near zero from a peak blood ethanol level may be a blood alcohol level of 0.03% or lower. In a separate embodiment, near zero from a peak blood ethanol level may be a blood alcohol level of 0.02% or lower. In another embodiment, near zero from a peak blood ethanol level may be a blood alcohol level of 0.015% or lower. In another embodiment, near zero from a peak blood ethanol level may be a blood alcohol level of 0.010% or lower. In another embodiment, near zero from a peak blood ethanol level may be a blood alcohol level of 0.005% or lower. In another embodiment, near zero from a peak blood ethanol level may be a blood alcohol level of 0.003% or lower. In another embodiment, near zero from a peak blood ethanol level may be a blood alcohol level of 0.001% or lower. In other embodiments, the blood aldehyde buildup associated with hangover syndrome occurs at a time following sufficient production or accumulation of aldehydes with a carbon chain length of more than 2 carbons. In yet some other embodiments, the blood aldehyde buildup associated with hangover syndrome occurs at a time following sufficient production or accumulation of aldehydes with a hydrophobicity greater than hydrophobicity of an acetaldehyde. In some embodiments, aldehydes with a hydrophobicity greater than hydrophobicity of an acetaldehyde may be aliphatic aldehydes with a carbon chain length of more than 2 carbons.

The invention also provides methods for attenuating facial flushing syndrome associated with consumption of alcoholic beverage(s) in a subject. In one embodiment, the method comprises administering an aldehyde sequestering agent so as to reduce or prevent counter blood acetaldehyde buildup and subsequent release of catecholamine and/or histamine resulting in facial flushing in the subject, thereby attenuating facial flushing syndrome associated with consumption of alcoholic beverage(s) in the subject. In a further embodiment, the acetaldehyde is produced from metabolism of ethanol in alcoholic beverage(s).

Examples of the alcoholic beverage(s) include, but are not limited to, bourbon, whiskey, scotch, wine, spirits, beer, vodka, gin and any alcoholic beverage(s) comprising ethanol but independent of aldehyde congener and fusel oil congener status.

In one embodiment, the facial flushing syndrome is associated with an ethnic group. In a further embodiment, the ethnic group is Asian or Asian descent.

In one embodiment, the facial flushing syndrome is associated with an ALDH2 deficiency. In a further embodiment, the ALDH2 deficiency produces a buildup of acetaldehyde from metabolism of ethanol in alcoholic beverage(s).

In one embodiment, the aldehyde sequestering agent is administered as dietary supplement. In another embodiment, the aldehyde sequestering agent is administered as a drug. In one embodiment, the aldehyde sequestering agent is formulated to be administered as a dietary supplement. In another embodiment, the aldehyde sequestering agent is formulated to be administered as a drug.

In one embodiment of the method for attenuating facial flushing syndrome associated with consumption of alcoholic beverage(s) in a subject, the method additionally comprises administering taurine, alpha-lipoic acid, pantethine, thiamine, 1-isothiocyano-4-(methylsulfinyl)butane (sulforaphane), glucosinolate precursor, glucosinolate, isothiocynate and extract of a cruciferous vegetable or a combination thereof. In a further embodiment, the taurine, alpha-lipoic acid, pantethine, thiamine, 1-isothiocyano-4-(methylsulfinyl)butane (sulforaphane), glucosinolate precursor, glucosinolate, isothiocynate and extract of a cruciferous vegetable or a combination thereof is administered as a dietary supplement.

In one embodiment, the taurine, alpha-lipoic acid, pantethine, thiamine, 1-isothiocyano-4-(methylsulfinyl)butane (sulforaphane), glucosinolate precursor, glucosinolate, isothiocynate and extract of a cruciferous vegetable or a combination thereof is administered together with the aldehyde sequestering agent at the same time. In another embodiment, they are administered separately from the aldehyde sequestering agent. In yet another embodiment, they are administered separately but at the same time, before or after administration of the aldehyde sequestering agent. In an additional embodiment, they are formulated with the aldehyde sequestering agent.

In one embodiment, the formulation is a dietary supplement. In another embodiment, the formulation is a drug.

In some embodiments of the invention as described above, the formulation comprises an immediate release component, a controlled release component or both.

The method further provides methods for decreasing risks of cardiovascular disease or cancer associated with a deficiency of ALDH2 in a subject. In one embodiment, the method comprises administering an aldehyde sequestering agent and/or an agent that functionally increases total activity of ALDH2 so as to reduce or counter aldehyde level in the subject, thereby decreasing risks of cardiovascular disease or cancer associated with a deficiency of ALDH2 in the subject. Examples of the agent that functionally increases total activity of ALDH2 include, but are not limited to, taurine, alpha-lipoic acid, pantethine, 1-isothiocyano-4-(methylsulfinyl)butane (sulforaphane), glucosinolate precursor, glucosinolate, isothiocynate and extract of a cruciferous vegetable or a combination thereof.

In one embodiment of the method, the subject consumes alcoholic beverage(s) and/or food. In a further embodiment, the food comprises lipids and fat.

In one embodiment, the aldehyde level is concentration of aldehyde present as an aldehyde congener or produced from metabolism of primary alcohol in the alcoholic beverage(s) by alcohol dehydrogenase. Examples of the primary alcohol include, but are not limited to, methanol, ethanol, isopentyl (isoamyl) alcohol, 2-methyl-1-butanol, isobutyl alcohol, n-propyl alcohol, 2-phenylethanol, butyl alcohol, hexanol and combination thereof.

In another embodiment, the aldehyde is produced by peroxidation of lipids by lipid peroxidases.

Examples of the aldehyde include, but are not limited to, formaldehyde, acetaldehyde, 3-methyl-1-butanal, 2-methyl-1-butanal, isobutanal, propanal, 2-phenylacetaldehyde, butanal, hexanal, 4-hydroxynonenal (4-HNE) and combination thereof.

In one embodiment, the cardiovascular disease is heart disease or atherosclerosis. In another embodiment, the cancer is alcohol-related cancer. Examples of the cancer include, but are not limited to, esophageal cancer, head and neck cancer, liver cancer, breast cancer, and colorectal cancer.

In one embodiment, the aldehyde sequestering agent is administered as dietary supplement. In another embodiment, the aldehyde sequestering agent is administered as a drug. In one embodiment, the aldehyde sequestering agent is formulated to be administered as a dietary supplement. In another embodiment, the aldehyde sequestering agent is formulated to be administered as a drug.

In one embodiment, the agent that functionally increases total activity of ALDH2 is administered as a dietary supplement. In another embodiment, the agent that functionally increases total activity of ALDH2 is administered as a drug.

In one embodiment, the aldehyde sequestering agent is administered together with the agent that functionally increases total activity of ALDH2 at the same time. In another embodiment, they are administered separately. In yet another embodiment, the agent that functionally increases total activity of ALDH2 is administered separately but at the same time, before or after administration of the aldehyde sequestering agent.

In one embodiment, the agent that functionally increases total activity of ALDH2 is formulated with the aldehyde sequestering agent. In another embodiment, the formulation is a dietary supplement. In yet another embodiment, the formulation is a drug.

In some embodiments of the invention as described above, the formulation additionally comprises an immediate release component, a controlled release component or both.

The invention provides methods for protecting or treating a subject exposed to environmental or occupational aldehyde(s). In one embodiment, the method comprises administering an aldehyde sequestering agent to the subject so as to sequester the aldehyde(s), thereby protecting or treating a subject exposed to environmental aldehyde(s).

In one embodiment, the method additionally comprises administering taurine, alpha-lipoic acid, pantethine, thiamine, 1-isothiocyano-4-(methylsulfinyl)butane (sulforaphane), glucosinolate precursor, glucosinolate, isothiocynate and extract of a cruciferous vegetable or a combination thereof. In a further embodiment, the taurine, alpha-lipoic acid, pantethine, thiamine, 1-isothiocyano-4-(methylsulfinyl)butane (sulforaphane), glucosinolate precursor, glucosinolate, isothiocynate and extract of a cruciferous vegetable or a combination thereof increases activity of ALDH2 to reduce or counteract aldehyde levels.

In one embodiment of the method, the environmental or occupational aldehyde(s) is introduced to the subject through inhalation or absorption through skin or eye. Examples of the environmental or occupational aldehyde(s) include, but are not limited to, formaldehyde, acetaldehyde, acrolein, glycolaldehyde and glutaraldehyde and combination thereof. In a further embodiment, the acrolein is associated with or produced by cigarette smoke, tobacco smoke, fried food, reheated fat, French fries and anticancer-agent, cyclophosphamide. In another embodiment, the glycolaldehyde is associated with or produced by ethylene glycol anti-freeze.

In some embodiments of the invention as described above, the aldehyde sequestering agent comprises a cysteine moiety comprising a thiol functional group and an amino functional group. [133] In a further embodiment, the thiol functional group and the amino functional group reacts with an aldehyde to form a cyclic 5-membered thiazolidine derivative. In yet a further embodiment, the thiazolidine derivative is a 2-substituted thiazolidine derivative wherein substituent at position 2 of thiazolidine ring corresponds to side chain of the aldehyde being sequestered.

Examples of the aldehyde sequestering agent include, but are not limited to, cysteinylglycine (CG), cystinyl-bis-glycine (CbG) and a combination thereof. In one embodiment, the amino acid of CG, CbG or a combination thereof is L-amino acid. In another embodiment, the amino acid of CG, CbG or a combination thereof is D-amino acid. In yet another embodiment, the amino acid of CG, CbG or a combination thereof is a mixture of L-amino acid and D-amino acid.

In some embodiments of the invention as described above, the amino acid is cysteine of CG or CbG.

In one embodiment of the method, the aldehyde sequestering agent produces a thiazolidine-4-carbonylglycine following sequestration of an aldehyde. In a further embodiment, the thiazolidine-4-carbonylglycine is a 2-substituted thiazolidine-4-carbonylglycine wherein substituent at position 2 of thiazolidine ring corresponds to side chain of the aldehyde being sequestered. In one further embodiment, the 2-substituted thiazolidine-4-carbonylglycine resulting from sequestering acetaldehyde is 2-methylthiazolidine-4-carbonylglycine (MTCG). In another further embodiment, the 2-substituted thiazolidine-4-carbonylglycine resulting from sequestering isoamyl aldehyde is 2-isobutylthiazolidine-4-carbonylglycine (BTCG).

In one embodiment of the invention as described above, examples of the alcoholic beverage(s) include, but are not limited to, bourbon, whiskey, scotch, wine, spirits, beer and any alcoholic beverage(s) comprising aldehyde congener and fusel oil congener.

In one embodiment of the invention as described above, the alcoholic beverage(s) comprises ethanol and a congener. Examples of the congener include, but are not limited to, fusel oil, acetic acid, ethyl acetate, alkyl acetate, aryl acetate, aldehyde, furfural and tannin. In one embodiment, the fusel oil is fusel alcohol and is a higher molecular weight alcohol than ethanol. Examples of the fusel oil include, but are not limited to, isopentyl (isoamyl) alcohol, 2-methyl-1-butanol, isobutyl alcohol, n-propyl alcohol, butyl alcohol, hexanol and combination thereof. In another embodiment, the congener is toxic or produces a toxic aldehyde.

In some embodiments of the invention as described above, the method comprises administering an aldehyde sequestering agent that functionally increases total activity of ALDH2 and/or taurine, alpha-lipoic acid, pantethine, 1-isothiocyano-4-(methylsulfinyl)butane (sulforaphane), glucosinolate precursor, glucosinolate, isothiocynate and extract of a cruciferous vegetable or a combination thereof. The administration of the agent is through consumption of a composition formulated as a dietary supplement or through drinking water or a beverage comprising a composition formulated for introduction to water or the beverage.

In practice, these compounds can be administered in unit dosage form comprising the active ingredient in combination with an acceptable carrier, which can be a solid, semi-solid, or liquid diluent. A unit dosage of the compound can also be administered without a carrier material. Examples of preparations include, but are not limited to, tablets, powders, capsules, aqueous solutions, suspensions including concentrates, liposomes, nano particles and other slow-releasing formulations, as well as transdermal delivery forms. Such techniques are known in the art and may be found in Remington's Pharmaceutical Sciences, Mack Publishing Co., Easton, Pa.

The compounds can be delivered by any suitable means, e.g., topically, orally, parenterally. Preferably, the delivery form is liquid or a solid such as a powder that can be stirred into an ingestible liquid. Standard carriers for topical, oral, or parenteral compositions may be used, many of which are described in Remington's Pharmaceutical Sciences, Mack Publishing Co., Easton, Pa.

For example, for oral administration, suitable carriers or diluents can include mannitol, lactose, starch, silicon dioxide, maltodextrin, citric acid, sodium bicarbonate, lecithin, microcrystalline cellulose, stearic, acid, magnesium stearate, talcum, glucose, and magnesium carbonate.

For parenteral administration, suitable carriers can include water, saline, dextrose, Ringer's solution, glycerol, and the like. Parenteral compositions can be in the form of suspensions, solutions, emulsions, and the like. Parenteral administration is usually by injection or infusion which can be subcutaneous, intramuscular, or intravenous.

Kits of the Invention

According to another aspect of the invention, kits are provided. Kits according to the invention include package(s) comprising compositions of the invention.

The phrase "package" means any vessel containing compounds or compositions presented herein. In preferred embodiments, the package can be a box or wrapping. Packaging materials for use in packaging products are well known to those of skill in the art. Examples of packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering active agents (e.g., an aldehyde sequestering agent so as to reduce or counter blood aldehyde buildup in a subject or an isolated aldehyde sequestering agent and an agent that functionally increases total activity of ALDH2) or compositions of the present invention to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include active agents in the solid phase or in a liquid phase (such as buffers provided) in a package. The kits also can include buffers for preparing solutions for conducting the methods, and pipettes for transferring liquids from one container to another.

The kit may optionally also contain one or more other compositions for use in combination therapies as described herein. In certain embodiments, the package(s) is a container for intravenous administration. In other embodiments, compounds are provided as a dietary supplement or a drug.

The following examples are presented to illustrate the present invention and to assist one of ordinary skill in making and using the same. The examples are not intended in any way to otherwise limit the scope of the invention.

EXAMPLES

Hangover syndrome may be a direct consequence of fusel alcohol congeners in alcoholic beverages, specifically their respective aldehyde metabolites, and ethanol, the major alcohol constituent in alcoholic beverages, or its aldehyde metabolite. On the other hand, the Asian flushing syndrome may be a direct consequence of in ability to further metabolize ethanol to acetaldehyde due reduced ALDH2 activity.

To find a naturally occurring compound capable of neutralizing aldehydes absorbed, inhaled, ingested or produced by a subject, we tested a cysteinylglycine (CG) dipeptide and its oxidized disulfide, cystinyl-bis-glycine (CbG), for their ability to sequester endogenously generated aldehydes.

Example 1

Sequestration of Metabolically-Generated Aldehydes

We examined cysteine (the natural "L" form), a semi-essential sulfhydryl amino acid, as a sequestering agent for acetaldehyde (Nagasawa et al., 1975). Indeed, cysteine readily condensed with acetaldehyde in aqueous solution to form a cyclic product, 2-methylthiazolidine-4 carboxylic acid (MTCA). Since we could not find MTCA in the urine of rats administered ethanol and L-cysteine, we administered MTCA itself at 400 mg/kg, and again, found no MTCA in the urine. We, therefore, prepared and administered radiolabeled MTCA ($^{14}$C at the 2-position) to a rat to follow its metabolic course (Nagasawa et al., 1984). To our surprise, most of the radiolabel appeared as expired $^{14}CO_2$. This indicated that in vivo, MTCA dissociated to cysteine and acetaldehyde, and the latter was metabolized to acetate, then to $CO_2$, the expected biochemical end-product from acetate.

"Cysteine-like" β-mercapto-α-amino acids with one or two bulky β-substituents may be required to sequester acetaldehyde in vivo (Cohen et al., 1999). Unfortunately, such amino acids do not occur in nature. However, there is a dipeptide of cysteine, viz., cysteinyglycine (CysGly), which is the catabolic product of glutathione following the γ-glutamylation of amino acids (Meister, 1984), that could potentially sequester metabolically-generated aldehydes. CysGly may be present in human plasma, in greater concentrations (100 μM) than glutathione itself (4 μM) (Kleinman and Ritchie, 2000), although Monsoor et al. (1996) reported approximately equal amounts being present. Also, its oxidized disulfide form, viz., cystinyl-bis-glycine, was found in human plasma as well (Jones et al., 1999; Monsoor et al., 1996).

In vitro, CysGly readily reacted with acetaldehyde at physiological pH and temperature to give 2-methylthiazolidine-4-carbonylglycine (MTCG), the dipeptide of MTCA and glycine (Kera et al., 1985; Anni et al., 2003). Indeed, Anni et al. showed that MTCG was stable in the biological fluids of rats, including urine, and was found in high concentrations (100 µM) in the bile of rats pretreated with ethanol and cyanamide, the latter, an inhibitor of ALDH. Although Anni et al. did not examine the urine of these rats for the presence of MTCG, Minet et al. (2011) (British American Tobacco), who were charged with developing assays for potential biomarkers present in the urine of cigarette smokers, such as the transformation products of acrylonitrile, formaldehyde, and acetaldehyde, developed an LC-MS/MS procedure for detecting MTCG in urine, and found amounts of MTCG in urine "sufficiently high" to interfere with measurements of the other urinary components from tobacco use. Indeed, Minet et al. suggested that this procedure could "be a better biomarker of acetaldehyde exposure through alcohol consumption". We feel that MTCG could be an especially useful marker to determine the amount of acetaldehyde exposure by individuals of Asian descent who are "flushers" and who drink alcoholic beverages (vide supra).

If the aldehydes produced by the oxidation of fusel alcohols can be sequestered by exogenously administered CysGly vis-a-vis cystinyl-bis-glycine (vide infra) to the corresponding 2-substituted thiazolidinecarbonylglycines, and then excreted into the urine, the hangover syndrome following excessive drinking of bourbon (or the like) should be greatly attenuated or eliminated completely. This presumes that sufficient CysGly is available at the time the fusel alcohols were being converted to their aldehydes. As mentioned earlier (vide supra), the time when blood alcohol reaches near zero (e.g., 0.04% or lower) can be estimated from the amount of alcohol consumed.

Cysteinylglycine Vis-A-Vis Cystinyl-Bis-Glycine

CysGly and its oxidized disulfide, cystinyl-bis-glycine, are found in human blood (Kleinman and Ritchie, 2000; Jones et al., 1999; Mansoor et al., 1992), the latter produced non-enzymatically from glutathione following the action of γ-glutamyl transpeptidase (Griffith and Tate, 1980). The invention herein provides that cellular CysGly can be augmented by supplying either CyGly or cystinyl-bis-glycine as dietary supplements, since they are redox equivalents and are interconvertible in vivo (vide infra). This should boost the blood/liver concentrations of CysGly sufficiently to sequester the aldehydes generated from the oxidative metabolism of the fusel alcohols.

There are a number enzyme systems that can reduce the disulfide bond of cystinyl-bis-glycine, although some are highly specific for certain substrates, e.g., glutathione reductase; others, like thioredoxin and thioredoxin reductase, appear to be less specific (Pader et al., 2014) Also, non-enzymatic thiol-disulfide exchange reactions are possible with endogenous thiols like GSH, cysteine and alpha-lipoic acid (dihydro form produced in vivo) to convert disulfides to their respective thiol forms. Reduction of the disulfide bond of cystinyl-bis-glycine in vivo would, of course, provide 2 mole equivalents of CysGly, i.e., cystinyl-bis-glycine serves as a biological precursor (i.e. a prodrug) of the latter.

Since CysGly is the by-product formed when GSH γ-glutamylates amino acids to transport them into cells, ubiquitous dipeptidases are present in cells to hydrolyze this dipeptide to recycle the cysteine and glycine. Dipeptidases are also required to hydrolytically remove the glycine moiety from pre-mercapturic acids, and Josch et al. (2003) have shown that cytosolic leucyl aminopeptidase (rat liver) is the major enzyme that hydrolyzes CysGly, cystinyl-bis-glycine and other S-substituted cysteinylglycines.

Nevertheless, exogenously administered CysGly or cystinyl-bis-glycine in bolus doses should overcome first pass metabolism to provide sufficient CysGly to sequester the aldehydes produced when the fusel alcohols are being metabolized by ADH.

Summary of Proposed Rat Study

A study will be conducted with rats administered disulfiram (Antabuse®), an inhibitor of ALDH2, and isoamyl alcohol as the prototype fusel alcohol. Cystinyl-bis-glycine will be administered orally to be converted in vivo to cysteinylglycine to sequester the aldehyde, isopentanal, formed from isoamyl alcohol. Urines from different groups will be collected for the quantitative measurement of the 2-substituted thiazolidinecarbonylglycines (2-substituted TCG's).

Example 2

A non-toxic substance produced endogenously, which can sequester the acetaldehyde derived from ethanol metabolism to a product that is readily excreted in the urine via the kidneys (or bile), is desirable for attenuating Asian flushing syndrome.

A dipeptide of L-cysteine, viz., cysteinylglycine (CysGly), where the free beta-mercapto and alpha-amino groups are ideally juxta-positional for condensation with acetaldehyde, has been shown to be present in human blood plasma (Mansoor et al., 1992; Kleinman and Ritchie, 2000; Jones et al., 2000). CysGly is a byproduct of glutathione when the latter is utilized for the transport of amino acids from the extracellular to the intracellular milieu by gamma-glutamylation of the amino acid to be transported (Meister, 1984). Moreover, CysGly has been shown to condense with AcH produced in vivo to form a 5-membered thiazolidine ring compound, viz., 2-methylthiazolidinecarbonylglycine (MTCG) (Kera et al., 1985; Anni et al., 2003). Indeed, MTCG has been found in the urine of rats exposed to acetaldehyde, and identification of this compound in urine has been suggested as a marker for acetaldehyde exposure (Minet et al., 2011, British American Tobacco).

Accordingly, Asians afflicted with this flushing syndrome that are anxious to avoid this flush and its health consequence, might ingest CysGly as a dietary supplement prior to drinking any alcoholic beverage in order to sequester the circulating AcH and attenuate this syndrome. Indeed, it may be desirable for this group of individuals to take this supplement on a daily basis to eliminate the toxic aldehydes such as 4-HNE produced in the metabolism of lipid peroxides.

Alternatively, the more stable disulfide form of CysGly, viz., cystinyl-bis-glycine (CbG), which is also present in human plasma (vide supra for references), may be substituted for CysGly. CbG is a non-enzymatic by-product when gamma-glutamyl transpeptidase interacts with CysGly (Grifith et al., 1980), and the two should be metabolically interconvertible in vivo.

Preliminary Studies

Although identified in urine, the long-term stability of MTCG in urine is still a question. MTCG is found to be stable in 0.1 N HCl, so we plan to collect the rat urine in acidified containers on ice. Presence of MTCG will be determined using a HPLC/MS method to obtain quantitative data of MTCG in rat urine. While the data of Kera et al. (1985) suggest some biliary excretion of MTCG, we will focus only on the presence of this product in urine.

Follow-Up

Dietary supplementation with CbG or CysGly will also allow the sequestration and elimination of 4-HNE, and protect against heart disease by those individuals with predisposition to cardiovascular ailments; especially, Asian flushers who lack a functional ALDH2.

It should be emphasized that this concept is also applicable for the sequestration of the aldehydes produced from the metabolism of the numerous fusel alcohols found in Scotch, bourbon, beer and wine, thus aborting the hangover syndrome following an evening of such alcohol abuse. CbG or CysGly could also protect hospital laboratory personnel who are chronically exposed to toxic aldehydes such as formaldehyde and glutaraldehyde in their workplaces.

This concept of sequestration and elimination of metabolically-derived, toxic aldehydes by the administration of substances such as CbG vis-à-vis CysGly, which are actually present endogenously, is original with us and applicable to a whole range of toxic aldehydes As alluded to above, such aldehydes are a) acetaldehyde which is poorly metabolized by nearly half of East Asians; b) other aldehydes such as 4-HNE generated in the peroxidative degradation of lipids, c) the aldehydes derived from short-chain alcohols present in certain alcoholic beverages, and d) tissue fixation agents used extensively in clinical laboratories.

Example 3

There are natural compounds, specifically, the dipeptide, cysteinylglycine (CG, see FIG. 1), that can sequester endogenously generated aldehydes to produce condensation products. Indeed, Kera et al. (1985) and Anni et al. (2003) have shown that CG condenses with the acetylaldehyde (AcH) produced from ethanol to give 2-methylthiazolidine-4-carbonylglycine (MTCG, see FIG. 1), which appears in the bile of rats given ethanol and cyanamide, the latter to inhibit ALDH (Anni et al, 2003).

CG Is an endogenous product produced when glutathione transfers its γ-glutamyl group to an amino acid to translocate the latter from extracellular to intracellular sites (Meister, 1984). These condensation products of CG with aldehydes are cyclic, 5-membered thiazolidine deriviatives, viz., 2-substituted thiazolidine-4-carbonylglycines, wherein the 2-substituents represent the side-chains of the corresponding aldehydes.

CG, as well as its oxidation product, cystinyl-bis-glycine (CbG, see FIG. 1), have been found in human blood plasma at concentrations similar to glutathione itself, i.e., approx. 4 μM (Kleinman and Ritchie 2000; Jones et al., 1999; Mansoor et al., 1992). CbG, the oxidized product of CG, is formed non-enzymatically when the latter interacts with γ-glutamyl transpeptidase (Griffith and Tate, 1980).

Experimental Results. We have now completed studies using rats, that verify that administration of CG or CbG to a subject fed ethanol or isoamyl alcohol results in production of aldehydes, such as acetaldehyde or isopentanal, which are sequestered by CG or CbG (following its conversion to CG) and subsequently eliminated from the subject. Sequestered products of CG (CG produced following reduction of CbG) and acetaldehyde or isopentanal, i.e., MTCG or isobutylthiazolidine-4-carbonylglycine (BTCG), respectively (see FIG. 1), may be detected in urine of these rats also administered an aldehyde dehydrogenase inhibitor, such as disulfiram or cyanamide.

In the first study, rats were administered disulfiram, an ALDH inhibitor and alcohol deterrent drug used to inhibit the metabolism of ethanol at the acetaldehyde stage, thus producing an adverse reaction that discourages further alcohol drinking (reviewed in Wikipedia, 2017). Treatment of rats with disulfiram causes a buildup of acetaldehyde in blood (Nagasawa et al, 1978). The rats were then administered CbG, orally, to determine whether CbG, following its in vivo conversion to CG, can sequester the acetaldehyde produced in the disulfiram-treated rats to a product that is excreted into the urine. Note that CbG in vivo may be reduced 2 CG. The product expected from this sequestration reaction is MTCG (vide supra). The MTCG in rat urine, collected over 24 hours following the ethanol dose, was quantitatively analyzed by LC/MS. We did not analyze the feces for MTCG, because of the complexities in measuring fecal contents. However, Anni et al. (2003) have shown that under similar conditions as our Group C animals (FIG. 2), the concentrations of MTCG in bile were high, viz. 90-100 μM.

CbG administration gave rise to the urinary excretion of MTCG which was 4.25 times greater than for CG administration (FIG. 2; compare Groups B and A). Since CbG produces 2 moles of CG. this was not unexpected. Rats receiving disulfiram and ethanol (Group C) appeared to excrete slightly more MTCG than the group receiving CG (Group A); however, this was not statistically significant (FIG. 2). We ascribe this to the poor oral bioavailability of CG and the endogenous presence of CG. Control rats receiving ethanol alone excreted only traces of MTCG, with 2 of 7 rats below the limit of detection (FIG. 2; Group D).

In the second study, isoamyl alcohol replaced ethanol, and cyanamide, another clinically-used ALDH inhibitor (Tottmar et al., 1977), replaced disulfiram to block the further metabolism of isoamyl aldehyde derived from isoamyl alcohol (FIG. 3). Isoamyl alcohol is the most abundant small, branched-chain alcohol congener present in bourbon (Damrau and Liddy, 1960). Whereas the group receiving cyanamide and isoamyl alcohol, but w/o CbG (Group B), were comatose (3 of 7) with one death suggestive of the toxicity of isoamyl aldehyde, the Group A animals receiving cyanamide, isoamyl alcohol and CbG, were normal although hypoactive. The control Group C where the animals received isoamyl alcohol and CbG, but no cyanamide to inhibit ALDH, were also normal but more active. The excreted product in urine here would be 2-isoobutylthiazolidine-4-carbonylglycine, viz., BTCG (FIG. 1). The urines were analyzed for BTCG by LC/MS as above.

FIG. 3 shows that only Group A animals excreted BTCG in the urine, albeit minimally. For Groups B and C animals, no BTCG could be detected in urine (below limits of detection, FIG. 3). Although the absolute values of BTCG were low in Group A animals compared to MTCG in the first study, the greater lipophilicity of BTCG over MTCG may favor excretion principally in the bile, hence reducing the amount excreted in the urine (Sharifi, M; Ghafourian, 2014; Luo, G. et al., 2010). Compared to the amount of MTCG detected in the urine of rats treated with disulfiram, CbG, and ethanol, the urinary excretion of BTCG in cyanamide-treated rats administered CbG and isoamyl alcohol is more than 3-orders of magnitude lower (nanograms of BTCG vs. micrograms of MTCG; compare FIGS. 2 and 3).

Conclusions. These results provide that CbG, which appears to be more orally bioavailable than CG and is converted to CG in vivo, and is able to sequester the whole series of toxic aldehydes discussed earlier, and serve as a universal aldehyde sequestering agent.

For example. the dreaded hangover following a bout of excessive drinking of bourbon (and the like) should be attenuated or prevented entirely by CbG—if taken before the imminent onset of the hangover. Since CbG is produced endogenously and found in human blood (vide supra), it would qualify as a dietary supplement. Also, CbG taken as a dietary supplement should serve as a protective agent for individuals exposed to formaldehyde and glutaraldehyde in the workplace.

In similar vein, Asians with a dysfunctional ALDH2, by taking CbG daily, may be able to avert heart disease by sequestering the toxic 4-hydroxynonenal produced in the peroxidation of dietary fat and preventing it from accumulating and binding to proteins. In addition, Asians with the alcohol flushing syndrome who are forced to drink alcohol because of intense social pressures—especially in Asian countries, may also be able to avert this alcoholic flush by taking CbG prior to drinking any alcoholic beverage.

REFERENCES

Amin, H.; Pristatsky, P.; Israel, Y. Binding of acetaldehyde to a glutathione metabolite: Mass spectrometric characterization of an aldehyde-cysteinylglycine conjugate. Alcohol. Clin. Exp. Res. 2003, 27(10), 1613-1621.

Anni, H.; Pristatsky, P.; Israel, Yedy. Binding of Acetaldehyde to a Glutathione Metabolite: Mass Spectrometric Characterization of an Acetaldehyde-Cysteinylglycine Conjugate. Alcohol. Clin. Exp. Res. 2003, 27(10), 1613-1621.

Anon., Disulfiram. Wikipedia (last edited on 9 May 2017).

Bendtsen, P.; Jones, A. W.; Helander, A. Urinary excretion of methanol and 5-hydroxytryptophol as biochemical markers of recent drinking in the hangover state. Alcohol Alcohol. 1998, 33(4) 431-438.

Bonte, W., Kuhnholz, B. Pharmacokinetics and metabolism of fusel alcohols. Proceedings $9^{th}$ International Conference on Alcohols, Drugs and Traffic Safety, San Juan, Puerto Rico, 1985, pp. 189-198.

Chen, C-H; Budas, G. R.; Churchill, E. N. et al. Activation of aldehyde dehydrogenase-2 reduces ischemic damage to the heart. Science 2008, 321: 1493-1495.

Cohen, J. F.; Elberling, J A.; DeMaster, E. G.; Lin, R. C.; Nagasawa, H. T. N-Terminal dipeptides of D(-)-Penicilamine as sequestration agents for acetaldehyde. J. Med, Chem. 2000, 43, 1029-1033.

Damrau, F.; Liddy, E. Hangovers and whisky congeners. Comparison of whisky with vodka. J. Nat. Med. Assoc. 1960, 52, 262-265.

Ekins, B. R; Rollins, D. E.; Duffy, D. P.; Gregory, M. C. Standardized treatment of severe methanol poisoning with ethanol and hemodialysis. West. J. Med. 1985, 142(3), 337-340.

Geodde, H. W.; Agrawal, D. P. Polymorphism of aldehyde dehydrogenase and alcohol sensitivity. Enzyme 1987, 37, 29-44.

Griffith, O. W.; Tate, S. S. The apparent glutathione oxidase activity of γ-glutamyl transpeptidase. J. Biol. Chem. 1980, 255(11), 5011-5014. Hirota, T.; Nishikawa, Y.; Komai, T.; Igarashi.; Kitagawa, H. Role of dehydropeptidase-1 in the metabolism of glutathione and its conjugates in rat kidney. Res, Commun. Chem, Path. Pharmacol. 1987, 56(2), 235-242.

Hori, H.; Fujii, W.; Hatanaka, T.; Suwa, Y. Effects of fusel oil on animal hangover models. Alcohol. Clin. Exp, Res. 2003, 27(8 Suppl) 37S-41S. Ingraham, J. L. Understanding congeners in wine. Wines and Vines. 2000, May issue.

Israel. Y.; Hurwitz, E.; Nlemela. O.; Arnon, R. Monoclonal and polyclonal antibodies against acetaldehyde containing epitopes in acetaldehyde-protein adducts. Proc. Natl. Acad. Sci. USA 1986, 83, 7923-7927.

Jones, D. P.; Carlson, J. L.; Mody, V. C. Jr.; Cai, J.; Lynn, M. J.; Sternberg, P., Jr. Redox status of glutathione in human plasma. 2000, 28, 625-635.

Josch, C.; Klotz; Sies, H. Identification of cytosolic leucyl aminopeptidase (EC 3.4.11.1) as the major cysteinylglycine-hydrolysing activity in rat liver. Biol/Chem. 2003, 384(2( ), 213-218.

Kapur, B. M.; Vandenbroucke, A. C.; Adamchik, Y.; Lohotay, D. C.; Carlen, P. L. Formic acid, a novel metabolite of chronic ethanol abuse, causes neurotoxicity, which is prevented by folic acid. Alcohol. Clin. Exp. Res. 2007, 31(12), 2114-2120.

Kera, Y.; Kiriyama, T.; Komura, S. Conjugation of acetaldehye with cysteinylglycine, the first metabolite in glutathione breakdown by γ-glutamyltranspeptidase. Agents and Actions, 1985, 17(1), 48-52.

Kleinman, W. A.; Ritchie, J. P. Status of glutathione and other thiols and disulfides in human plasma. Biochem. Pharmacol. 2000, 60, 19-29.

Lieber, C. S. The discovery of the microsomal ethanol oxidizing system and its physiological and pathologic role. Drug Metab. Rev. 2004, 36, 511-529.

Luo, G.; Johson, S.; Hsueh, M-M. Zheng, J.; Cai, H.; Xin, B; Chong, S.; He, K.; Harper, T. W. In Silico Prediction of Biliary Excretion of Drugs in Rats Based on Physicochemical Properties. Drug Metab. Disp. 2010, 38(3), 422-430.

Majchrowicz, E; Mendelson, J. H. Blood methanol concentrations during experimentally induced ethanol intoxication in alcoholics. J. Pharmacol. Exp. Therap. 1971, 179, 293-300.

Mansoor, M. A.; Svardal, A. M.; Ueland, P. M. Determination of the redox status of cysteine, cysteinylglycine, homocysteine, and glutathione in human plasma. Anal. Biochem. 1992, 200, 218-229.

Medina, V. A.; Donahue, T. M.; Sorrell. M. F.; Tuna, D. J, Covalent binding of acetaldehyde to hepatic proteins during ethanol oxidation. J Lab Clin Med. 1985, 105(1), 5-10. Meister, A. New aspects of glutathione biochemi.stry and transport: selective alteration of transport. Fed. Proc. 1984, 43. 3031-3042.

Minet, E.; Cheung, F.; Errington, G.; Sterz, K.; Scherer, G. An evaluation of CEMA, and adducts of cysteinylglycine as potential biomarkers of exposure to acrylonitrile, formaldehyde, and acetaldehyde from cigarette smoke. $65^{th}$ TSRC. Lexington, Ky. Sep. 19, 2011. bat-science.com.

Nagasawa, H. T. N-Terminal D(-)-penicillamine peptides as aldehyde sequestering agents. U.S. Pat. No. 6,686,336 B2, Feb. 3, 2004.

Nagasawa, H. T.; Elberling, J. A.; DeMaster, E. G. Structural Requirements for the Sequestration of Metabolically-generated Acetaldehyde. J. Med. Chem. 1980, 23, 140-143.

Nagasawa, H. T.; Elberling, J. A.; Roberts, J. C. β-Substituted Cysteines as Sequestering Agents for Ethanol-Derived Acetaldehyde In Vivo. J. Med. Chem. 1987, 30, 1373-1378.

Nagasawa, H. T.; Goon, D. J. W.; Constantino, N. V.; Alexander, C. S. Diversion of Ethanol Metabolism by Sulfhydryl Amino Acids. D-Penicillamine-directed Excretion of 2,5,5-Trimethyl-D-thiazolidine-4-carboxylic Acid in the Urine of Rats after Ethanol Administration. Life Sci. 1975, 17, 707-713.

Nagasawa, H. T.; Goon, D. J. W.; DeMaster, E. G.; Alexander, C. S. Lowering of Ethanol-Derived Circulating Blood Acetaldehyde in Rats by D-Penicillamine. Life Sci. 1977, 20, 187-194.

Nagasawa, H. T.; Goon, D. J. W.; DeMaster, E. G. 2, 5,5-Trimethylthiazolidine-4-carboxylic Acid, a D(−)-Penicillamine-directed Pseudometabolite of Ethanol. Detoxication Mechanism for Acetaldehyde. J. Med. Chem. 1978, 21, 1274-1279.

Nagasawa, H. T.; Goon, D. J. W.; Zera, R. T.; Yuzon, D. L. Prodrugs of L-cysteine as liver protective agents. 2(R, S)-Methylthiazolidine-4(R)-carboxylic Acid, a latent cysteine. J. Med. Chem. 1982, 25, 489-491.

Nagasawa, H. T.; Goon, D. J. W.; Muldoon, W. P.; Zera, R. 2-Substituted Thiazolidine-4R-Carboxylic Acids as Prodrugs of L-Cysteine. Protection of Mice Against Acetaminophen Hepatotoxicity. J. Med. Chem., 1984, 27, 591-596.

Nagasawa, H. T.; Shirota, F. N.; DeMaster, E. G. Alcoholism: Aldehyde Dehydrogenase Inhibitors as Alcohol Deterrent Agents. Biomedical Chemistry/Applying Chemical to the Principles Understanding and Treatment of Disease 1999, 73-79.

Nishimura, Y.; Kato, Y.; Kohmura, Y.; Ueda, Y. Process for producing cysteinylfgycine-enriched food material and process for producing flavor-enhancement agent. U.S. Pat. No. 7,108,884 B2. Sep. 19, 2006.

Pader, I.; Sengupta, R.; Cebula, M.; Xu, J.; Lundberg, J. O.; Holmgren, A.; Johansson, K.; Amer, E. S. Thioredoxin-related protein of 14 kDa is an efficient L-cystine reductase and S-denitrolase Proc. Natl. Acad. Sci. USA, 2014, 111(19), 6964-6969.

Prat, G.; Adam, A.; Sanchez-Turet, M.; Alcohol hangover: a critical review of explanatory factors. Hum. Psychopharmacol. 2009, 24(4), 259-267.

Reischl, R. J.; Bicker, W.; Keller, T.; Lamprecht, G.; Lindner, W. Occurrence of 2-methylthiazolildine-4-carboxylic acid, a product of cysteine and acetaldehyde, in human blood as a consequence of ethanol consumption. Ann, Bioanal. Chem. 2012, 404, 1779-1787.

Rohsenow, D. J.; Howland, J.; Amedt, J. I.; Almeida, A. B.; Greece, J.; Minsky, S.; Kempler, C. S.; Sales, S. Intoxication with bourbon verses vodka: effects on hangovers, sleep, and next-day neurocognitive performance in young adults. 2010, 34(3), 509-513.

Rohsenow, D. J.; Howland, J. The role of beverage congeners in hangover and other residual effects of alcohol intoxication: A review. Current Drug Abuse Reviews. 2010, 3, 76-79.

Roth, K. Chemistry of a hangover—alcohol and its consequences. Chemistry Views, Parts 1, 2, 3. Jul. 9, 2011.

Sharifi, M; Ghafourian, T. Estimation of biliary excretion of foreign compounds using properties of molecular structure. AAPS J. 2014, 16(1), 65-78.

Sjodin, K.; Nilsson, E.; Hallberg. A.; Tunek, A. Metabolism of N-acetyl-L-cysteine. Biochem. Pharmacol. 1989, 22, 3981-3989.

Ushida, Y. and Talalay, P. Sulforaphane accelerates acetaldehyde metabolism by inducing aldehyde dehydrogenases: Relevance to ethanol intolerance. Alcohol and Alcoholism. 2013, 48(5), 526-534.

Strittmatter, P.; Ball, E. G. Formaldehyde dehydrogenase, a glutathione dependent enzyme system. J. Biol. Chem. 1955, 213(1), 445-461.

Tottmar, O.; Marchner, H.; Lindberg, P. in Alcohol and Aldehyde Metabolism Systems (Eds. Thurman, R. G.; Wiliamson, J. R.; Droth, H. R.; and Chance, B. Vol. II, p. 203. Academic Press, New York (1977).

Woo, Y. S.; Moon, S. J.; Lee, H. K.; Chae, J. H.; Lee, C. T.; Kim, D. J. Concentration changes of methanol in blood samples during an experimentally induced alcohol hangover state. Addict. Biol. 2005, 10(4), 351-355.

Yoshida, A.; Huang, I.-Y.; Ikawa, M. Molecular abnormality of an inactive aldehydedehydrogenase variant commonly found in Orientals. Proc. Natl. Acad, Sc. (USA) 1984, 81, 258. Wikipedia. Disulfiram (last edited on 9 May 2017).

What is claimed is:

1. A method for treating a hangover associated with consumption of an alcoholic beverage(s) in a subject comprising administering an aldehyde sequestering agent in an effective amount so as to reduce or counter blood aldehyde buildup in the subject in need thereof, wherein the aldehyde sequestering agent is cystinyl-bis-glycine, a pharmaceutically acceptable salt thereof, or a hydrate thereof, thereby treating the hangover in the subject.

2. The method of claim 1, wherein the alcoholic beverage(s) comprise one or more congener(s).

3. The method of claim 2, wherein the congener is selected from the group consisting of an aldehyde, a fusel oil, and a combination thereof.

4. The method of claim 3, wherein the fusel oil comprises a mixture of two or more alcohols.

5. The method of claim 4, wherein the fusel oil is a fermentation product comprising C3 or higher chain length aliphatic alcohols.

6. The method of claim 3, wherein the fusel oil comprises two or more alcohols selected from the group consisting of isopentyl (isoamyl) alcohol, 2-methyl-1-butanol, isobutyl alcohol, n-propyl alcohol, butyl alcohol, hexanol and a combination thereof.

7. The method of claim 3, wherein the congener is an aldehyde congener selected from the group consisting of acetaldehyde, furfural, an alkyl aldehyde, an aryl aldehyde, and a combination thereof.

8. The method of claim 1, wherein cysteine in cystinyl-bis-glycine is L-cysteine.

9. A method for attenuating facial flushing syndrome associated with consumption of an alcoholic beverage(s) in a subject comprising administering an aldehyde sequestering agent so as to reduce or counter blood acetaldehyde buildup and subsequent release of catecholamine and/or histamine resulting in facial flushing in the subject in need thereof, wherein the aldehyde sequestering agent is cystinyl-bis-glycine, a pharmaceutically acceptable salt thereof, or a hydrate thereof, thereby attenuating facial flushing syndrome associated with consumption of the alcoholic beverage(s) in the subject.

10. The method of claim 9, wherein the facial flushing syndrome is associated with an aldehyde dehydrogenase 2 (ALDH2) deficiency.

* * * * *